(12) United States Patent
Kumar et al.

(10) Patent No.: US 11,231,417 B2
(45) Date of Patent: Jan. 25, 2022

(54) REAGENT STORAGE IN AN ASSAY DEVICE

(71) Applicant: Meso Scale Technologies, LLC., Rockville, MD (US)

(72) Inventors: Sudeep Kumar, Hackettstown, NJ (US); George Sigal, Rockville, MD (US); Michael Tsionsky, Derwood, MD (US)

(73) Assignee: Meso Scale Technologies, LLC., Rockville, MD (US)

( * ) Notice: Subject to any disclaimer, the term of this patent is extended or adjusted under 35 U.S.C. 154(b) by 0 days.

(21) Appl. No.: 16/815,598

(22) Filed: Mar. 11, 2020

(65) Prior Publication Data
US 2020/0209234 A1 Jul. 2, 2020

Related U.S. Application Data

(60) Division of application No. 15/206,656, filed on Jul. 11, 2016, now Pat. No. 10,627,399, which is a continuation of application No. 13/272,350, filed on Oct. 13, 2011, now abandoned.

(60) Provisional application No. 61/455,112, filed on Oct. 14, 2010.

(51) Int. Cl.
*G01N 33/543* (2006.01)
*G01N 33/53* (2006.01)
*C12Q 1/6823* (2018.01)
*C12Q 1/6832* (2018.01)
*C12Q 1/6834* (2018.01)

(52) U.S. Cl.
CPC ..... *G01N 33/54386* (2013.01); *C12Q 1/6823* (2013.01); *C12Q 1/6832* (2013.01); *C12Q 1/6834* (2013.01); *G01N 33/5306* (2013.01); *G01N 2446/00* (2013.01); *G01N 2458/30* (2013.01)

(58) Field of Classification Search
CPC ......... G01N 33/54386; G01N 33/5306; G01N 2446/00; G01N 2458/30; C12Q 1/6823; C12Q 1/6832; C12Q 1/6834
See application file for complete search history.

(56) References Cited

U.S. PATENT DOCUMENTS

| | | | |
|---|---|---|---|
| 4,168,146 A | 9/1979 | Grubb et al. |
| 4,235,601 A | 11/1980 | Deutsch et al. |
| 4,366,241 A | 12/1982 | Tom et al. |
| 4,442,204 A | 4/1984 | Greenquist et al. |
| 5,093,268 A | 3/1992 | Leventis et al. |
| 5,147,806 A | 9/1992 | Kamin et al. |
| 5,208,535 A | 5/1993 | Nakayama et al. |
| 5,236,849 A | 8/1993 | Ishikawa |
| 5,238,808 A | 8/1993 | Bard et al. |
| 5,240,863 A | 8/1993 | Shibue et al. |
| 5,308,754 A | 5/1994 | Kankare et al. |
| 5,324,457 A | 6/1994 | Zhang et al. |
| 5,541,623 A | 7/1996 | Engstrom |
| 5,589,136 A | 12/1996 | Northrup et al. |
| 5,591,581 A | 1/1997 | Massey et al. |
| 5,597,910 A | 1/1997 | Gudibande et al. |
| 5,641,623 A | 6/1997 | Martin |
| 5,643,713 A | 7/1997 | Liang et al. |
| 5,679,519 A | 10/1997 | Oprandy |
| 5,705,402 A | 1/1998 | Leland et al. |
| 5,731,147 A | 3/1998 | Bard et al. |
| 5,776,672 A | 7/1998 | Hashimoto et al. |
| 5,786,141 A | 7/1998 | Bard et al. |
| 5,846,485 A | 12/1998 | Leland et al. |
| 5,866,434 A | 2/1999 | Massey et al. |
| 5,888,834 A | 3/1999 | Ishikawa et al. |
| 6,066,448 A | 5/2000 | Wohlstadter et al. |
| 6,136,268 A | 10/2000 | Ala-Kleme et al. |
| 6,207,369 B1 | 3/2001 | Wohlstadter et al. |
| 6,214,552 B1 | 4/2001 | Heroux et al. |
| 6,939,720 B2 | 9/2005 | Chandler et al. |
| 7,807,448 B2 | 10/2010 | Glezer et al. |
| 2003/0003464 A1 | 1/2003 | Phan et al. |
| 2003/0027352 A1 | 2/2003 | Hooper et al. |
| 2004/0009528 A1 | 1/2004 | Shaw et al. |
| 2004/0189311 A1 | 9/2004 | Glezer et al. |
| 2006/0211055 A1 | 9/2006 | Hafeman et al. |
| 2006/0234253 A1 | 10/2006 | Hasui et al. |
| 2006/0263907 A1 | 11/2006 | Zweig |
| 2006/0275852 A1 | 12/2006 | Montagu et al. |
| 2007/0031283 A1 | 2/2007 | Davis et al. |
| 2007/0202538 A1 | 8/2007 | Glezer et al. |
| 2010/0075311 A1 | 3/2010 | Barrault et al. |
| 2011/0201099 A1 | 8/2011 | Anderson et al. |

(Continued)

FOREIGN PATENT DOCUMENTS

| JP | 2606722 B2 | 2/1997 |
|---|---|---|
| JP | 2006-517652 A | 7/2006 |

(Continued)

OTHER PUBLICATIONS

Golla R. et al., "A Sensitive, Robust High-Throughput Electrochemiluminescence Assay for Rat Insulin", Journal of Biomolecular Screening 9(1):62-70 (2004).

Hochman J. et al., "An Active Antibody Fragment (Fv) Composed of the Variable Portions of Heavy and Light Chains", Biochemistry 12(6):1130-1135 (1973).

Kijek T.M. et al., "Rapid and Sensitive Immunomagnetic-Electrochemiluminescent Detection of Staphyloccocal Enterotoxin B", Journal of Immunological Methods 236:9-17 (2000).

(Continued)

*Primary Examiner* — Narayan K Bhat
(74) *Attorney, Agent, or Firm* — Scully, Scott, Murphy & Presser, P.C.

(57) ABSTRACT

The invention relates to methods for conducting binding assays in an assay device that includes one or more storage and use zone. The storage zones of the assay device are configured to house one or more reagents used in an assay conducted in the use zone of the device.

31 Claims, 26 Drawing Sheets

(56) References Cited

U.S. PATENT DOCUMENTS

| | | |
|---|---|---|
| 2012/0157332 A1 | 6/2012 | Kumar et al. |
| 2013/0316928 A1 | 11/2013 | Kumar et al. |
| 2016/0349253 A1 | 12/2016 | Kumar et al. |

FOREIGN PATENT DOCUMENTS

| | | |
|---|---|---|
| WO | 97/36931 A1 | 10/1997 |
| WO | 98/12539 A1 | 3/1998 |
| WO | 98/57154 A1 | 12/1998 |
| WO | 99/14599 A1 | 3/1999 |
| WO | 99/32662 A1 | 7/1999 |
| WO | 99/58962 A1 | 11/1999 |
| WO | 99/63347 A2 | 12/1999 |
| WO | 00/03233 A1 | 1/2000 |
| WO | 03/031591 A2 | 4/2003 |
| WO | 2004/061418 A2 | 7/2004 |
| WO | 2007/014267 A2 | 2/2007 |
| WO | 2008/016680 A2 | 2/2008 |
| WO | 2009/126828 A2 | 10/2009 |
| WO | 2012/051386 A2 | 4/2012 |

OTHER PUBLICATIONS

Mathew BC et al., "An Overview of Electrocheminescent (ECL) Technology in Laboratory Investigations", Kathmandu University Medical Journal 3(1), Issue 9:91-93 (2005).

Miao W., "Electrogenerated Chemiluminescence and its Biorelated Applications", Chem. Rev. 108:2506-2553 (2008).

Pauling L., "Molecular Architecture and Biological Reactions", Chemical and Engineering News 24(10):1375-1377 (May 25, 1946).

Porter R.R. et al., "Subunits of Immunoglobulins and Their Relationship to Antibody Specificity", J. Cell Physiol 67, Sup. 1:51-64(1966).

Tian D. et al., "Sandwhich-Type Electrochemiluminescence Immunosensor Based on N-(Aminobutyl)-N-Ethylisoluminol Labeling and Gold Nanoparticle Amplification", Talanta 78:399-404 (2009).

Watson et al., "Molecular Structure of Nucleic Acids—A Structure for Deoxyribose Nucleic Acid", Nature 171:737-738 (Apr. 25, 1953).

Japanese Notice of Reasons for Rejection dated Jun. 30, 2015 received from Japanese Application No. 2013-533995, together with an English-language translation.

International Search Report and Written Opinion dated Jan. 21, 2011 received from the Korean Intellectual Property Office from related PCT/US2010/030664.

International Search Report and Written Opinion dated May 23, 2012 received from the Korean Intellectual Property Office from related PCT/US2011/056095.

Canadian Examination Report dated Aug. 10, 2017 received in Canadian Application No. 2,814,680.

Extended Supplementary European Search Report dated Jul. 22, 2014 received from related European Application No. 11833390.5.

European Office Action dated Jul. 19, 2017 received in European Application No. 11 833 390.5.

European Communication dated Mar. 2, 2018 received in European Application No. 11 833 390.5.

European Summons to Attend Oral Proceedings dated Jan. 21, 2019 received in European Application No. 11 833 390.5.

U.S. Office Action dated May 23, 2019 in U.S. Appl. No. 15/206,656.

U.S. Final Office Action dated Oct. 12, 2018 in U.S. Appl. No. 15/206,656.

U.S. Office Action dated May 10, 2018 in U.S. Appl. No. 15/206,656.

U.S. Office Action dated Jan. 11, 2016 in U.S. Appl. No. 13/272,350.

U.S. Final Office Action dated Jun. 24, 2015 in U.S. Appl. No. 13/272,350.

U.S. Final Office Action dated Mar. 10, 2015 in U.S. Appl. No. 13/272,350.

U.S. Office Action dated Sep. 16, 2014 in U.S. Appl. No. 13/272,350.

U.S. Final Office Action dated Jul. 15, 2013 in U.S. Appl. No. 13/272,350.

U.S. Office Action dated Aug. 10, 2012 in U.S. Appl. No. 13/272,350.

Canadian Examination Report dated Oct. 21, 2020 received in Canadian Application No. 2,814,680.

Extended European Search Report dated Mar. 26, 2020 received in European Application No. 19 17 4836.7.

European Communication dated Mar. 31, 2021 received in European Application No. 19 174 836.7.

REAGENT STORAGE IN AN ASSAY DEVICE

CROSS-REFERENCE TO RELATED APPLICATIONS

The present application is a divisional of U.S. patent application Ser. No. 15/206,656, filed Jul. 11, 2016, which is a continuation of U.S. patent application Ser. No. 13/272,350, filed Oct. 13, 2011, now abandoned, which claims the benefit of U.S. Provisional Application No. 61/455,112, filed Oct. 14, 2010, the disclosure of which is incorporated herein by reference in its entirety.

FIELD OF THE INVENTION

Improved methods for conducting binding assays are provided. These methods include a pre-concentration step to improve assay performance, for example, by increasing the concentration of analyte in the sample and/or by reducing the concentration of extraneous materials that may be present in the sample which may hinder the performance of the binding assay.

BACKGROUND OF THE INVENTION

A substantial body of literature has been developed concerning techniques that employ binding reactions, e.g., antigen-antibody reactions, nucleic acid hybridization and receptor-ligand reactions, for the sensitive measurement of analytes of interest in samples. The high degree of specificity in many biochemical binding systems has led to many assay methods and systems of value in a variety of markets including basic research, human and veterinary diagnostics, environmental monitoring and industrial testing. The presence of an analyte of interest may be measured by directly measuring the participation of the analyte in a binding reaction. In some approaches, this participation may be indicated through the measurement of an observable label attached to one or more of the binding materials.

There is always a desire to improve binding assays and devices used to conduct binding assays by increasing the signal obtained from a binding event, reducing non-specific binding, and/or improving measurement accuracy and precision, especially when analyzing complex biological samples.

SUMMARY OF TILE INVENTION

The invention provides an assay device including (a) a storage zone comprising a surface-reagent complex confined to the storage zone, the surface-reagent complex comprising (i) a reagent linked to a first targeting agent; and (ii) a surface linked to a second targeting agent, wherein the reagent and the surface are linked, in the surface-reagent complex, via a releasable binding interaction between the first and second targeting agents; and (b) one or more use zones each configured to use the reagent in an assay for an analyte of interest in a sample. The assay device of the invention may include one or more storage zones and/or one or more use zones. Additionally, the storage zone may also include two or more surface-reagent complexes, each including a distinct assay reagent that may be used in an assay conducted in the one or more use zones. For example, the storage zone also includes a second surface-reagent complex confined to the storage zone, the second surface-reagent complex comprising (i) a second reagent linked to a third targeting agent; and (ii) a second surface linked to a fourth targeting agent, wherein the second reagent and the second surface are linked, in the second surface-reagent complex, via a second releasable binding interaction between the third and fourth targeting agents; and the one or more use zones are further configured to use the second reagent in the assay. The use zones may each comprise two or more assay regions each configured to use the reagent(s) stored in the storage zone in one or more assays conducted with a sample in the assay device.

The device may be used to conduct a plurality of assays for one or more analytes present in the sample, e.g., a first assay region of the one or more use zones are each configured to conduct an assay for a first analyte of interest in the sample and an additional assay region in the one or more use zones is configured to conduct an assay for an additional analyte of interest in the sample. Alternatively, a first assay region of the one or more use zones is configured to conduct a first assay for the analyte of interest in the sample and an additional assay region of the one or more use zones is configured to conduct a second assay for the analyte of interest in the sample.

The invention also provides a multiplexed assay device comprising (a) a storage zone comprising a surface-reagent complex confined to the storage zone, the surface-reagent complex comprising (i) a reagent linked to a first targeting agent; and (ii) a surface linked to a second targeting agent, wherein the reagent and the surface are linked, in the surface-reagent complex, via a releasable binding interaction between the first and second targeting agents; and (b) one or more use zones each comprising a plurality of assay regions configured to use the reagent in a multiplexed assay for a plurality of analytes in a sample. A first assay region of the one or more use zones is configured to conduct an assay for a first analyte of interest in the sample and an additional assay region in the one or more use zones is configured to conduct an assay for an additional analyte of interest in the sample. In addition, the storage zone may further comprises a second surface-reagent complex confined to the storage zone, the second surface-reagent complex comprising (i) a second reagent linked to a third targeting agent; and (ii) a second surface linked to a fourth targeting agent, wherein the second reagent and the second surface are linked, in the second surface-reagent complex, via a second releasable binding interaction between the third and fourth targeting agents; and the one or more use zones are further configured to use the second reagent in the multiplexed assay.

The invention further provides a method of conducting an assay in an assay device as described herein, including the steps: (x) introducing the sample to the one or more use zones; (y) subjecting the storage zone to a condition that releases the reagent from the surface-reagent complex; (z) transferring the reagent from the storage zone to the one or more use zones; and (xx) conducting the assay in the one or more use zones with the reagent. If the use zones are each configured to use a second reagent in an assay, the method further comprises, prior to the conducting step, subjecting the storage zone to an additional condition that releases the second reagent from the second surface-reagent complex; and transferring the second reagent from the storage zone to the one or more use zones.

A method of using such an assay device may also include the steps of (x) introducing the sample to the one or more use zones; (i) subjecting the storage zone to a condition that releases the reagent from the surface-reagent complex; (ii) subjecting the storage zone to a condition that releases the second reagent from the second surface-reagent complex; (y) transferring the reagent from the storage zone to the first assay region; (z) transferring the second reagent from the storage zone to the second assay region; (xx) conducting an assay in the first assay region with the reagent; and (yy) conducting an assay in the second assay region with the second reagent. The transferring steps may be simultaneous or sequential. Similarly, the conducting steps may also be simultaneous or sequential.

In addition, the invention provides a method of using an assay device of the invention including the steps: (x) introducing the sample to the one or more use zones; (y) subjecting the storage zone to a condition that releases the reagent from the surface-reagent complex; (z) transferring the reagent from the storage zone to the first assay region and the second assay region; (xx) conducting the assays in the first and second assay regions, respectively. The assays may be conducted simultaneously or sequentially.

In another embodiment, the assay device of the invention may be used in the conduct of an assay by (x) introducing the sample to the one or more use zones via the storage zone; (y) adding a diluent to the storage zone and (i) subjecting the storage zone to a condition that releases the reagent from the surface-reagent complex; (ii) subjecting the storage zone to an additional condition that releases the second reagent from the second surface-reagent complex; (z) transferring the reagent and the second reagent from the storage zone to the first and second assay regions; (xx) conducting the assays in the first and second assay regions. The assays and/or transfer steps may be conducted simultaneously and/or sequentially.

Still further, the assay device may be used in an assay by (x) introducing the sample to the one or more use zones via the storage zone; (y) adding a diluent to the storage zone and (i) subjecting the storage zone to a condition that releases the reagent from the surface-reagent complex; (ii) subjecting the storage zone to an additional condition that releases the second reagent from the second surface-reagent complex; (z) transferring the reagent from the storage zone to the first assay region; (xx) transferring the second reagent from the storage zone to the second assay region; (yy) conducting the assays in the first and second assay regions. The assays and/or transfer steps may be conducted simultaneously and/or sequentially.

Moreover, the invention provides a multiplexed assay device comprising (a) a storage zone comprising (i) a first reagent linked to a surface in the storage zone via a first releasable binding interaction; (ii) a second reagent linked to a second surface in the storage zone via a second releasable binding interaction; (b) a first use zone configured to use the first reagent in an assay for a first analyte; and (c) a second use zone configured to use the second reagent in an assay for a second analyte. The first releasable binding interaction comprises a linkage between a first targeting agent and a second targeting agent, wherein the first targeting agent is linked to the reagent and the second targeting agent is linked to the surface. Moreover, the reagent and the surface are linked to form a surface-reagent complex, wherein the surface-reagent complex is confined to the storage zone. The second releasable binding interaction comprises a linkage between a third targeting agent and a fourth targeting agent, wherein the third targeting agent is linked to the second reagent and the fourth targeting agent is linked to the second surface, and the second reagent and the second surface are linked to form a second surface-reagent complex, wherein the second surface-reagent complex is confined to the storage zone. Such a multiplexed assay device comprises a fluidic network, such that the storage zone and the first and second use zones are in fluidic communication, wherein the network is configured to direct fluid in the storage zone to the first use zone, the second use zone, or both. The network is configured to direct fluid to the first use zone and the second use zone sequentially or simultaneously. The first and second reagents are each confined in the storage zone to distinct regions of the storage zone. The first and second releasable binding interactions require the same or different conditions to release the first and second reagents respectively, from the first and second surfaces of the storage zone, e.g., subjecting the storage zone to increased or decreased temperature, pH changes, an electric potential, a change in ionic strength, competition, and combinations thereof. Moreover, each of the first and second use zones comprise a plurality of assay regions each configured to use the first and second reagents in a multiplexed assay for a plurality of different analytes in a sample.

Also provided is a method of conducting a multiplexed assay using the multiplexed assay device described herein including (a) introducing a sample comprising the first and second analytes to the first and second use zones; (b) subjecting the storage zone to a condition that releases the first reagent from the storage zone; (c) transferring the first reagent from the storage zone to at least one of the first and second use zones; and (d) conducting one or more assays for at least one of the first and second analytes.

The method may also include the steps of subjecting the storage zone to an additional condition that releases the second reagent from the storage zone and transferring the second reagent from the storage zone to at least one of the first and second use zones, and optionally washing at least one of the first and second use zone prior to the transferring step.

Also provided is a method of conducting a multiplexed assay in a multiplexed assay device including (a) introducing a sample comprising the first and second analytes to the first and second use zones; (b) subjecting the storage zone to a condition that releases the first reagent from the storage zone; (c) transferring the first reagent from the storage zone to the first use zone; (d) subjecting the storage zone to a condition that releases the second reagent from the storage zone; (e) transferring the second reagent from the storage zone to the second use zone; and (f) conducting assays for the first and second analytes in the first and second use zones. The method may also include washing the first and second use zones prior to the transferring step (c), and the assays may be conducted simultaneously or sequentially.

BRIEF DESCRIPTION OF DRAWINGS

The accompanying drawings are provided to illustrate rather than limit the scope of the invention. Throughout the accompanying Figures, "P" refers to a particle to which one or more moieties are attached; "S" refers to a first solid phase; "A" refers to a target analyte; "C" refers to contaminants; and "*" refers to a detectable label linked to an assay component.

FIG. 5(a) shows magnetic concentration of analytes using colloids coated with anti-antibodies against the analytes and also coated with ECL labels. Multiple antibodies may be used to bind different analytes. FIG. 5(b) shows detection of the analyte-colloid complexes in a sandwich immunoassay format.

FIGS. 7(a)-(b) show an assay device including one storage zone that houses a surface-reagent complex that supplies reagent to use zones 1 and 2, while FIG. 7(c) shows an assay device including multiple storage zones that each lead to a use zone. In 7(c), sample and liquid reagent compartments in the assay device are in fluid communication with the storage and use zones.

DETAILED DESCRIPTION OF THE INVENTION

Figure 1A:
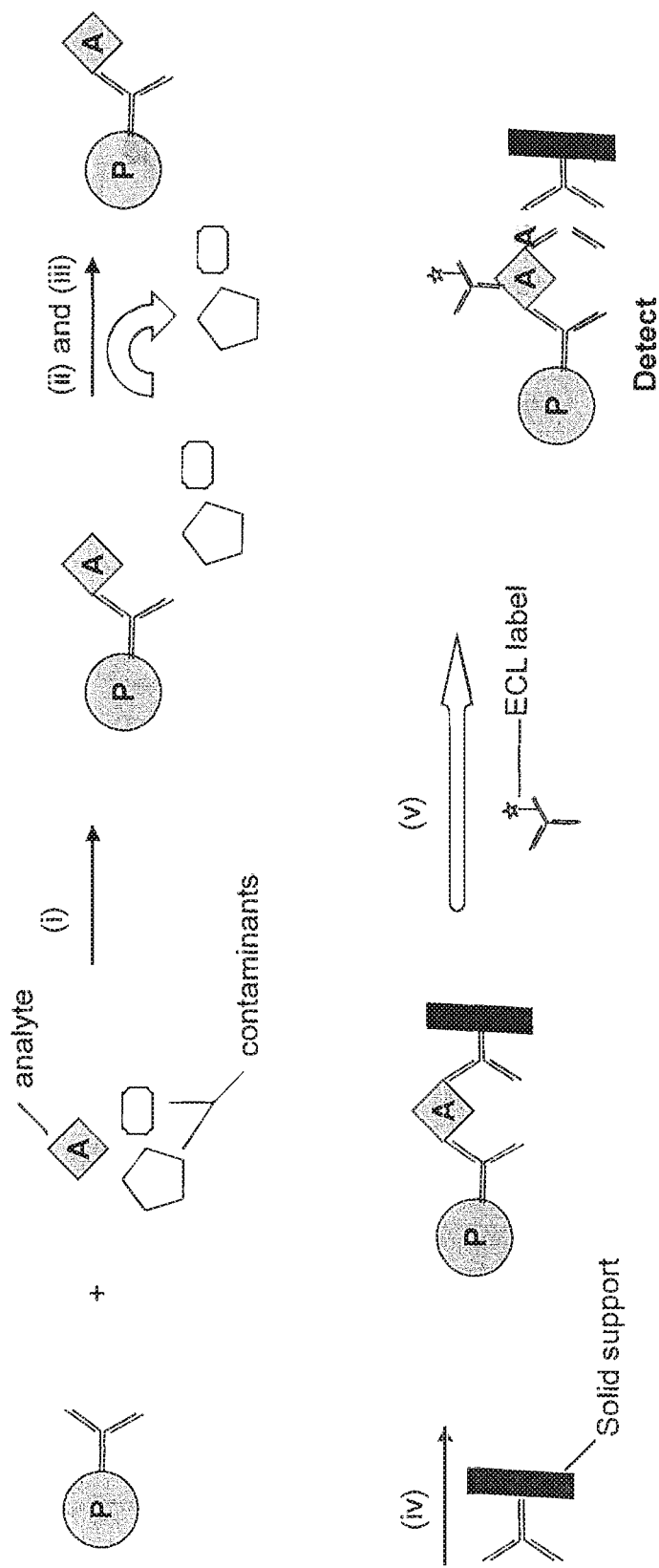
FIGS. 1(a)-1(e) illustrate various assay formats in which a particle is used as an assay component.

The present invention provides improved solid phase binding assays that include a collection, separation and/or release step. The methods of the present invention improve assay performance by allowing for pre-concentration of an analyte in a sample and/or by reducing or eliminating the amount of contaminants in a sample that may hinder the performance of the assay, e.g., by interfering with the detection step and/or by non-specifically binding with one or more of the components in the mixture.

(i) Samples/Analytes

Examples of samples that may be analyzed by the methods of the present invention include, but are not limited to food samples (including food extracts, food homogenates, beverages, etc.), environmental samples (e.g., soil samples, environmental sludges, collected environmental aerosols, environmental wipes, water filtrates, etc.), industrial samples (e.g., starting materials, products or intermediates from an industrial production process), human clinical samples, veterinary samples and other samples of biological origin. Biological samples that may be analyzed include, but are not limited to, feces, mucosal swabs, physiological fluids and/or samples containing suspensions of cells. Specific examples of biological samples include blood, serum, plasma, feces, mucosal swabs, tissue aspirates, tissue homogenates, cell cultures and cell culture supernatants (including cultures of eukaryotic and prokaryotic cells), urine, saliva, sputum, and cerebrospinal fluid.

Analytes that may be measured using the methods of the invention include, but are not limited to proteins, toxins, nucleic acids, microorganisms, viruses, cells, fungi, spores, carbohydrates, lipids, glycoproteins, lipoproteins, polysaccharides, drugs, hormones, steroids, nutrients, metabolites and any modified derivative of the above molecules, or any complex comprising one or more of the above molecules or combinations thereof. The level of an analyte of interest in a sample may be indicative of a disease or disease condition or it may simply indicate whether the patient was exposed to that analyte.

The assays of the present invention may be used to determine the concentration of one or more, e.g., two or more analytes in a sample. Thus, two or more analytes may be measured in the same sample. Panels of analytes that can be measured in the same sample include, for example, panels of assays for analytes or activities associated with a disease state or physiological conditions. Certain such panels include panels of cytokines and/or their receptors (e.g., one or more of TNF-alpha, TNF-beta, IL1-beta, IL2, IL4, IL6, IL-10, IL-12, IFN-y, etc.), growth factors and/or their receptors (e.g., one or more of EGF, VGF, TGF, VEGF, etc.), drugs of abuse, therapeutic drugs, vitamins, pathogen specific antibodies, auto-antibodies (e.g., one or more antibodies directed against the Sm, RNP, SS-A, SS-alpha, J0-1, and Scl-70 antigens), allergen-specific antibodies, tumor markers (e.g., one or more of CEA, PSA, CA-125 II, CA 15-3, CA 19-9, CA 72-4, CYFRA 21-1, NSE, AFP, etc.), markers of cardiac disease including congestive heart disease and/or acute myocardial infarction (e.g., one or more of Troponin T, Troponin I, myoglobin, CKMB, myeloperoxidase, glutathione peroxidase, β-natriuretic protein (BNP), alpha-natriuretic protein (ANP), endothelin, aldosterone, C-reactive protein (CRP), etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease (alpha-amyloid, beta-amyloid, Aβ 42, Aβ 40, Aβ 38, Aβ 39, Aβ 37, Aβ 34, tau-protein, etc.), markers of osteoporosis (e.g., one or more of cross-linked N or C-telopeptides, total deoxypyridinoline, free deoxypyridinoline, osteocalcin, alkaline phosphatase, C-terminal propeptide of type I collagen, bone-specific alkaline phosphatase, etc.), markers of fertility state or fertility associated disorders (e.g., one or more of Estradiol, progesterone, follicle stimulating hormone (FSH), lutenizing hormone (LH), prolactin, hCG, testosterone, etc.), markers of thyroid disorders (e.g., one or more of thyroid stimulating hormone (TSH), Total T3, Free T3, Total T4, Free T4, and reverse T3), and markers of prostrate cancer (e.g., one or more of total PSA, free PSA, complexed PSA, prostatic acid phosphatase, creatine kinase, etc.). Certain embodiments of invention include measuring, e.g., one or more, two or more, four or more or 10 or more analytes associated with a specific disease state or physiological condition (e.g., analytes grouped together in a panel, such as those listed above; e.g., a panel useful for the diagnosis of thyroid disorders may include e.g., one or more of thyroid stimulating hormone (TSH), Total T3, Free T3, Total T4, Free T4, and reverse T3).

The methods of the present invention are designed to allow detection of a wide variety of biological and biochemical agents, as described above. In one embodiment, the methods may be used to detect pathogenic and/or potentially pathogenic virus, bacteria and toxins including biological warfare agents ("BWAs") in a variety of relevant clinical and environmental matrices, including and without limitation, blood, sputum, stool, filters, swabs, etc. A non-limiting list of pathogens and toxins that may be analyzed (alone or in combination) using the methods of the present invention is *Bacillus anthracis* (anthrax), *Yersinia pestis* (plague), *Vibrio cholerae* (cholera), *Francisella tularensis* (tularemia), *Brucella* spp. (Brucellosis), *Coxiella burnetii* (Q fever), orthopox viruses including variola virus (smallpox), viral encephalitis, Venezuelan equine encephalitis virus (VEE), western equine encephalitis virus (WEE), eastern equine encephalitis virus (EEE), Alphavirus, viral hemorrhagic fevers, Arenaviridae, Bunyaviridae, Filoviridae, Flaviviridae, Ebola virus, staphylococcal enterotoxins, ricin, botulinum toxins, *Clostridium botulinum*, mycotoxin, *Fusarium, Myrotecium, Cephalosporium, Trichoderma, Verticimonosporium, Stachybotrys*, glanders, wheat fungus, *Bacillus globigii, Serratia marcescens*, yellow rain, trichothecene mycotoxins, *Salmonella typhimurium*, aflatoxin, *Xenopsylla cheopis, Diamanus montanus*, alastrim, monkeypox, Arenavirus, Hantavirus, Lassa fever, Argentine hemorrhagic fevers, Bolivian hemorrhagic fevers, Rift Valley fever virus, Crimean-Congo virus, Hanta virus, Marburg hemorrhagic fevers, yellow fever virus, dengue fever viruses, influenza (including human and animal strains including H5N1 avian influenza), human immunodeficiency viruses I and II (HIV I and II), hepatitis A, hepatitis B, hepatitis C, hepatitis (non-A, B or C), Enterovirus, Epstein-Barr virus, Cytomegalovirus, herpes simplex viruses, *Chlamydia trachomatis, Neisseria gonorrheae, Trichomonas vaginalis*, human papilloma virus, *Treponema pallidum, Streptococcus pneumonia, Haemophilus influenzae, Mycoplasma pneumoniae, Chlamydophila pneumoniae, Legionella pneumophila, Staphylococcus aureus, Moraxella catarrhalis, Streptococcus pyogenes, Clostridium difficile, Neisseria meningitidis, Klebsiella pneumoniae, Mycobacterium tuberculosis*, coronavirus, Coxsackie A virus, rhinovirus, parainfluenza virus, respiratory syncytial virus (RSV), metapneumovirus, and adenovirus.

(ii) Binding Reagents

The skilled artisan in the field of binding assays will readily appreciate the scope of binding agents and companion binding partners that may be used in the present methods. A non-limiting list of such pairs include (in either order) oligonucleotides and complements, receptor/ligand pairs, antibodies/antigens, natural or synthetic receptor/ligand pairs, amines and carbonyl compounds (i.e., binding through the formation of a Schiff's base), hapten/antibody pairs, antigen/antibody pairs, epitope/antibody pairs, mimitope/antibody pairs, aptamer/target molecule pairs, hybridization partners, and intercalater/target molecule pairs.

The binding assays of the methods of the present invention may employ antibodies or other receptor proteins as binding reagents. The term "antibody" includes intact antibody molecules (including hybrid antibodies assembled by in vitro re-association of antibody subunits), antibody fragments, and recombinant protein constructs comprising an antigen binding domain of an antibody (as described, e.g., in Porter, R. R. and Weir, R. C. J. *Cell Physiol.*, 67 (Suppl); 51-64 (1966) and Hochman, 1. Inbar, D. and Givol, D. *Biochemistry* 12: 1130 (1973)), as well as antibody constructs that have been chemically modified, e.g., by the introduction of a detectable label.

Binding reagents and binding partners that are linked to assay components to enable the attachment of these assay components to each other or to solid phases may be described herein as "targeting agents". For targeting agents that work in pairs, e.g., antigen-antibody, oligonucleotides-complement, etc., one targeting agent of the pair may be referred to herein as the first targeting agent, whereas the companion targeting agent may be referred to as the second targeting agent. In certain embodiments, these targeting agents are selected based on the reversibility of their binding reactions. In particular, targeting agent pairs may be selected, e.g., because under a first set of conditions the pair will bind to form a binding complex which, under a second set of conditions, can be caused to dissociate to break apart the complex, e.g., by subjecting bound targeting agent pairs to increased or decreased temperature, changes in chemical environment or assay buffer (e.g., ionic strength changes, pH changes, addition of denaturants, changes in light or electrical potential, etc.), adding competing binding reagents that compete with one targeting agent for binding to another targeting agent, and combinations thereof. Suitable conditions may be derived through routine experimentation. There are many well-established cleavable chemical linkers that may be used that provide a covalent bond that may be cleaved without requiring harsh conditions. For example, disulfide containing linkers may be cleaved using thiols or other reducing agents, cis-diol containing linkers may be cleaved using periodate, metal-ligand interactions (such as nickel-histidine) may be cleaved by changing pH or introducing competing ligands. The terms "cleave" or "cleaving" are also used herein to refer to processes for separating linked assay components that do not require breaking covalent bonds, e.g., there are many well-established reversible binding pairs and conditions that may be employed (including those that have been identified in the art of affinity chromatography). By way of example, the binding of many antibody-ligand pairs can be reversed through changes in pH, addition of protein denaturants or chaotropic agents, addition of competing ligands, etc.

The targeting agents may be pairs of oligonucleotides comprising complementary sequences. The preferred length is approximately 5 to 100 bases, preferably, approximately, 10 to 50 bases, and more preferably approximately 10 to 2.5 bases. In addition, the targeting oligonucleotides sequences need not be identical in length and in certain embodiments it may be beneficial to provide one targeting oligonucleotide sequence that is longer than its binding partner, e.g., by up to 25 bases, or up to 15 bases, or up to 10 bases. Known methods that are commonly employed for strand separation employ i) temperatures above the melting temperature for the complex, ii) use an alkaline pH of 11 (or higher) or a low pH; iii) use high ionic strength and/or iv) use nucleic acid denaturants such as formamide. Other methods for strand separation include the use of helicase enzymes such as Rep protein of *E.coli* that can catalyse the unwinding of the DNA, or binding proteins such as 32-protein of *E. coli* phage T4 that act to stabilize the single-stranded form of DNA. In specific embodiments, dissociation of complementary nucleic acid strands is accomplished by exposing the strands to elevated temperature greater than 60° C.

The methods of the present invention may be used in a variety of assay devices and/or formats. The assay devices may include, e.g., assay modules, such as assay plates, cartridges, multi-well assay plates, reaction vessels, test tubes, cuvettes, flow cells, assay chips, lateral flow devices, etc., having assay reagents (which may include targeting agents or other binding reagents) added as the assay progresses or pre-loaded in the wells, chambers, or assay regions of the assay module. These devices may employ a variety of assay formats for specific binding assays, e.g., immunoassay or immunochromatographic assays. Illustrative assay devices and formats are described herein below. In certain embodiments, the methods of the present invention may employ assay reagents that are stored in a dry state and the assay devices/kits may further comprise or be supplied with desiccant materials for maintaining the assay reagents in a dry state. The assay devices preloaded with the assay reagents can greatly improve the speed and reduce the complexity of assay measurements while maintaining excellent stability during storage. The dried assay reagents may be any assay reagent that can be dried and then reconstituted prior to use in an assay. These include, but are not limited to, binding reagents useful in binding assays, enzymes, enzyme substrates, indicator dyes and other reactive compounds that may be used to detect an analyte of interest. The assay reagents may also include substances that are not directly involved in the mechanism of detection but play an auxiliary role in an assay including, but not limited to, blocking agents, stabilizing agents, detergents, salts, pH buffers, preservatives, etc. Reagents may be present in free form or supported on solid phases including the surfaces of compartments (e.g., chambers, channels, flow cells, wells, etc.) in the assay modules or the surfaces of colloids, beads, or other particulate supports.

In one embodiment, assay reagents may be provided in an assay device that includes one or more regions or zones used for reagent storage. These storage zones may include the reagent bound to a surface within the storage zone, such that the reagent is confined within that zone until it is subjected to conditions sufficient to release the reagent for use elsewhere in the device. For example, the storage zone may include a surface-reagent complex comprising a reagent linked to a first targeting agent and a surface linked to a second targeting agent, wherein the reagent and the surface are linked in the surface-reagent complex, via a releasable binding interaction between the first and second targeting agents. In this embodiment, the reagent is released from the surface-reagent complex and the storage zone by subjecting the storage zone to conditions sufficient to disrupt the releasable binding interaction between the first and second targeting agents. As described herein, those conditions may include but are not limited to, subjecting the storage zone to increased or decreased temperature, light, altering the pH of that zone, applying an electrical potential, changes in ionic strength, adding a competitor, and combinations thereof.

The surface to which the second targeting agent, and thereby, the reagent, is linked, may be any solid support that can be incorporated within or confined to the storage zone. For example, the surface may be the surface of one or more particles, as described herein, present in the storage zone. Alternatively, the surface is a surface of the storage zone, for example, a surface of a compartment, channel, conduit, well, etc., within the storage zone. Preferably, the storage zone surface is roughened or includes one or more raised features or indentations that increase the relative surface area within the storage zone available to hold surface-reagent complexes. In one embodiment, the storage zone surface includes surface area-enhancing features that increase the surface area, such that the surface area accessible to a component capable of binding to that surface is at least two-fold larger than the surface area of a flat surface. In a preferred embodiment, the surface area accessible for binding is at least three-fold larger than the surface area of a flat surface. The high surface area support can be provided by roughening a surface or otherwise providing three dimensional texture to a surface. A variety of established approaches for preparing roughened or textured surfaces will be available to one skilled in the art. Included in these approaches is the production of surfaces with high aspect ratio features such as arrays of columns that are prepared through conventional machining, micro-machining or lithography (e.g., approaches using LIGA or other microfabrication technologies as described in U.S. Pat. Nos. 5,707,799 and 5,952,173) or injection molding.

The storage zone surface may also include a composite material comprising exposed particles distributed in a matrix. The composite material may include, but is not limited to, carbon particles, graphitic particles, or carbon nanotubes, Optionally, the composite may be etched (e.g., by chemical or plasma etching) to expose more particles and increase the surface roughness. In one specific example, the surface is provided by a printed carbon ink. In another embodiment, the storage zone surface may include a porous support that provides an enhanced surface area through the surface area available in its pores. Such porous supports include porous membranes (such as filtration membranes and lateral flow membranes) and gels. Preferred gels include hydrogels. A number of suitable hydrogels are well established as supports for reagents, as are chemistries for linking reagents to hydrogels, for applications such as affinity chromatography, solid phase synthesis of biological polymers and binding assays, in applications. Examples of such hydrogels include, but are not limited to, polymers of sugars (polysaccharides), acrylic acid, acrylates, acrylamides, ethylene glycol, propylene glycol. The hydrogels may be cross-linked and/or may be co-polymers of different monomer components.

An assay device that incorporates a storage zone for reagents also includes a use zone configured to use those reagents in an assay conducted in that device. Therefore, once the reagent is released from the surface-reagent complex, free reagent is available for use in an assay conducted in the use zone. Free reagent is transferred from the storage zone to the use zone, wherein it can participate in an assay for an analyte of interest. That assay may involve one or more additional reagents present in the use zone or otherwise supplied to the use zone. In one embodiment, the use zone may include one or more additional reagents bound to a solid support within the use zone and/or dried on a surface of the use zone. In a specific embodiment, the reagent is a binding reagent capable of binding an analyte of interest in a sample, and the use zone includes an additional ti reagent, bound to a solid support within the use zone, wherein that additional reagent also binds the analyte of interest. In this embodiment, the analyte present in the sample binds to the surface of the use zone via the additional reagent, as well as to the free reagent transferred from the storage zone to form a sandwich complex. The binding reagent may include a detectable label, e.g., an ECL label, and the analyte may be detected in the use zone by detecting the presence or absence of the label, e.g., via measuring electrochemiluminescence emitted in the use zone. The sample may be introduced to the use zone directly or the sample is first introduced to the storage zone and thereafter, the sample flows from the storage zone to the use zone. The reagent may be released prior to contacting the storage zone with sample or after the storage zone is contacted with sample. In one embodiment, sample is introduced to the storage zone, which is then subjected to conditions required for release of the reagent from the surface-reagent complex. Thereafter, the sample and the free reagent are optionally incubated prior to transferring the sample-reagent mixture to the use zone.

Figures 7A, 7B, 7C:
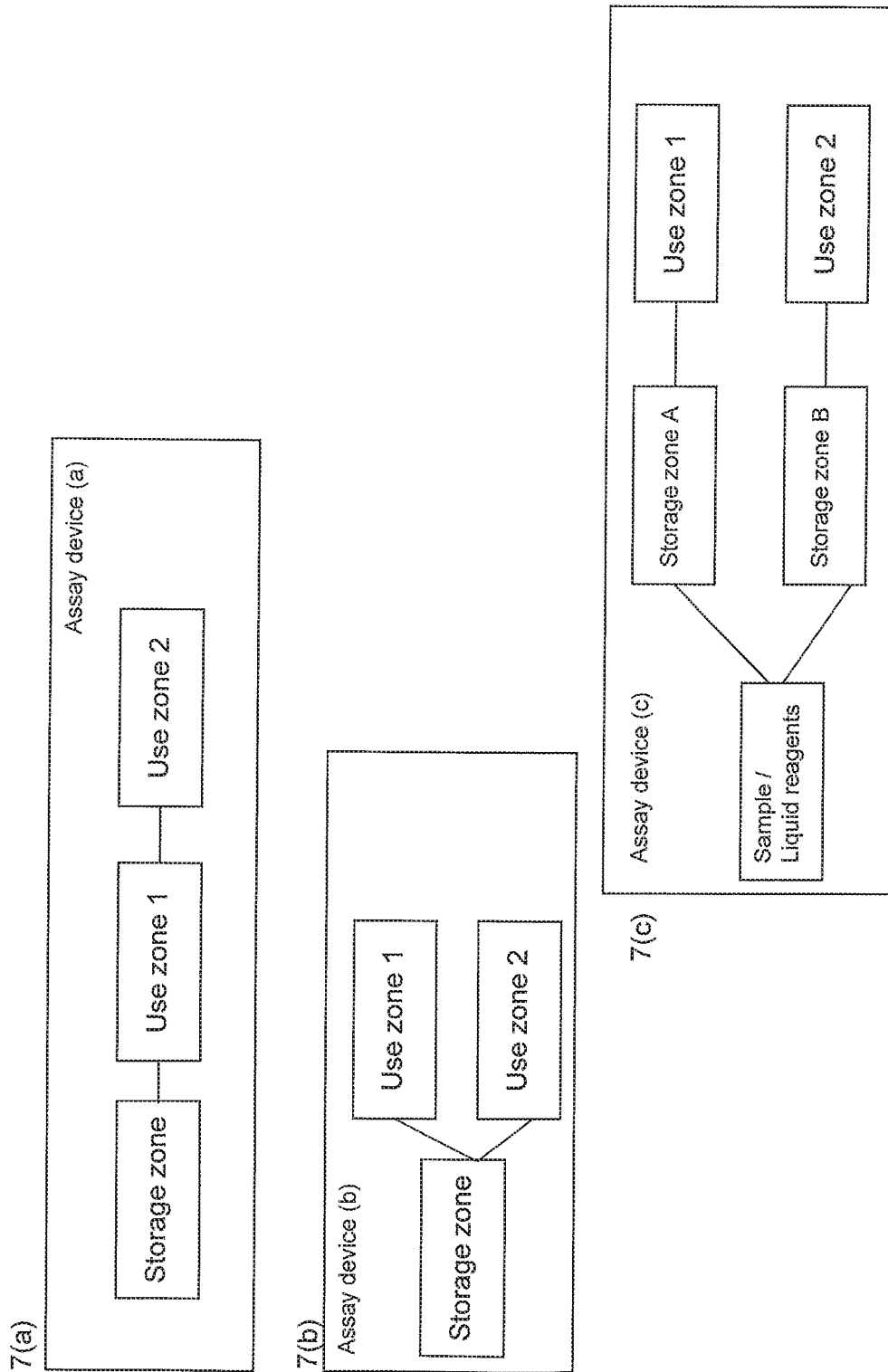
FIG. 7(a)-7(c) illustrate three alternative embodiments of an assay device include one or more storage zones and one or more use zones.
Figures 8A, 8B, 8C, 8D, 8E, 8F:
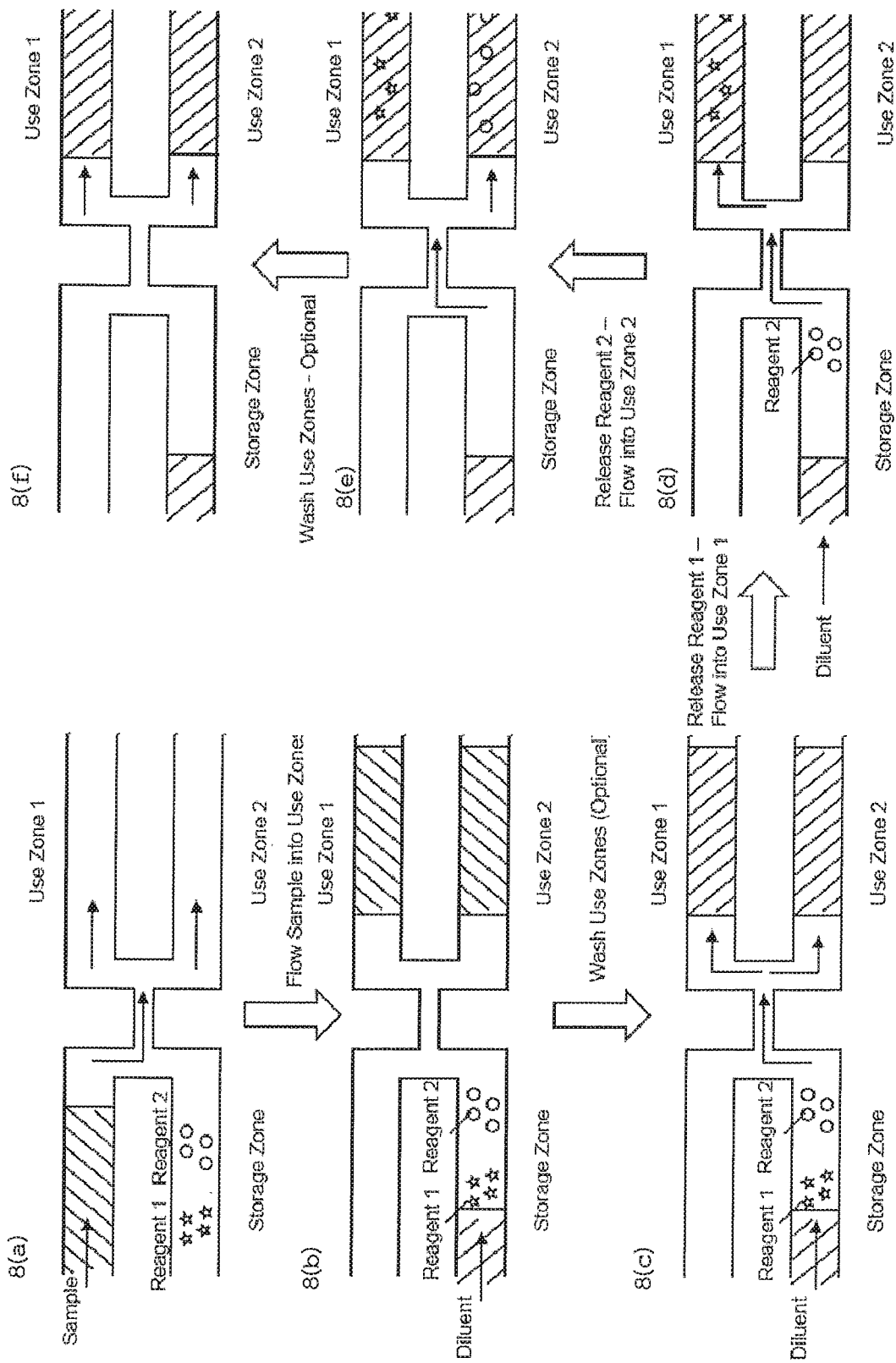
FIGS. 8(a)-8(f) illustrate the use of an alternate assay device of the present invention.

In a preferred embodiment, the storage zone and the use zone are in fluidic communication along a fluid path. For example, the assay device may be a cartridge and the storage zone and the use zone are positioned within the cartridge along a fluid path. Examples of this embodiment are shown in FIG. 7(a)-(c). In FIG. 7(a), the assay device includes a storage zone and at least two use zones and each of the storage zones and use zones are in fluid communication. The use zones may be configured in the assay device in series, as shown in FIG. 7(a) or in parallel, as shown in FIG. 7(b). FIG. 7(c) shows yet another configuration of an assay device including multiple storage and use zones. In the embodiment shown in FIG. 7(c), the storage and use zones are also in fluidic communication with sample and/or reagent compartments within the assay device.

Another embodiment is shown in FIGS. 8(a)-8(f). The assay device of FIGS. 8(a)-8(f) includes a storage zone including a first surface-reagent complex and a second surface-reagent complex and at least two use zones, wherein the storage zone and the use zone are in fluidic communication via a fluidic network. Sample is introduced into a compartment of the device in panel (a) and the fluidic network carries that sample to the use zones, as shown in panel (b). Panels (b) and (c) also shows that diluents can be passed through the storage zone (under conditions that do not release the surface-reagent complexes) and carried through the fluidic network to the use zones to provide an optional wash of the use zones. Diluent is then passed through the storage zone while subjecting the storage zone to a condition that releases the first reagent, which is then carried to the fluidic network in to use zone 1, as shown in panel (d). The second reagent is then released by a second set of conditions and carried, via flow of diluents through the microfluidic network, to use zone 2, as shown in panel (e). Finally, the use zones are optionally washed to remove excess reagent, as shown in panel (f).

In one embodiment, the storage zone and use zones are included within a fluidic network further comprising one or more vent ports in fluidic communication with the storage and use zones (directly or through vent conduits) so as to allow the equilibration of fluid in the zones with the atmosphere or to allow for the directed movement of fluid into or out of a specified zone by selectively sealing, opening (to atmospheric pressure) or applying positive or negative pressure to specific vent ports.

In another embodiment, the assay device is a multi-well assay plate and the use zone is positioned within a well of the plate, while the storage zone is located on a supplemental surface of the well that does not overlap with the use zone.

In a further embodiment, the assay device may include one or more surface-reagent complexes in the storage zone. In the embodiment depicted in FIG. 8, for example, the storage zone includes a first surface-reagent complex (as described above) and also includes a second surface-reagent complex confined to the storage zone, the second surface-reagent complex including (i) a second reagent linked to a third targeting agent; and (ii) a second surface linked to a fourth targeting agent, wherein the second reagent and the second surface are linked, in the second surface-reagent complex, via a second releasable binding interaction between the third and fourth targeting agents; and the use zone is further configured to use the second reagent in the assay. The various reagents stored within the storage zone may be used in one or more assays conducted in the use zone, or each of the reagents stored within the storage zone may be used in each of the assays conducted in the use zone. The reagents stored within the storage zone may be selectively released, one of the reagents may be released from the surface-reagent complex composition by a first set of conditions that differ from a second set of conditions used to release another reagent stored in the storage zone.

Additionally, the use zone may include two or more assay regions each configured to use the reagents stored within the storage zone in one or more assays conducted with a single sample in the device. In one embodiment, the use zone includes a first assay region configured to conduct an assay for a first analyte of interest in a sample and the use zone may also include an additional assay region configured to conduct an assay for an additional analyte of interest that may also be present in the sample. Alternatively, the first assay region in the use zone may be used to conduct a first assay for an analyte, while another assay region in the use zone may be used to conduct a second assay for the same analyte. Still further, the assay device may include a plurality of use zones each configured to use the reagents stored within the storage zone in one or more assays conducted with a single sample in the device. Each use zone may include one or more assay regions as described above. Moreover, the assay device may include a plurality of storage zones, e.g., for each use zone there is a corresponding storage zone. Various configurations of an assay device including multiple use zones and/or storage zones are shown in FIG. 7(a)-(c) and FIGS. 8(a)-8(f).

As described above, a storage zone may include a plurality of different reagents as surface-reagent complexes. In one embodiment different reagents are held in the storage zone by different releasable binding reactions that are cleaved under different conditions. Therefore, by subjecting each defined region of the storage zone to the appropriate conditions, each reagent is selectively released from the storage zone. The different reagents may be in surface-reagent complexes that are inter-mixed or held in distinct regions of the storage zone. As described herein, those conditions may include but are not limited to, subjecting the region to increased or decreased temperature, light, altering the pH of that region, changing the ionic strength, applying an electrical potential, adding a competitor, and combinations thereof. By using binding reactions cleaved under different conditions, it is possible to selectively release one reagent at a time from surface-reagent complexes in the storage zone. For example, one reagent may be selectively released by heating while another may be selective released by changing pH or one reagent may be selectively released using a first competitor while another may be selectively released using a second competitor. In another embodiment, different reagents may be released one a time using different releasable binding reactions that require increasingly stringent cleavage conditions (such as increasing temperature, increasing or decreasing pH, increasing competitor concentration, increasing levels of light, increasing or decreasing ionic strength, etc.). For example, a first reagent may be released at a first temperature level and a second reagent may be subsequently released at a second higher temperature level.

In another embodiment, the storage zone may include a plurality of defined spatial regions, at least two of the different regions holding different reagents in surface-reagent complexes that hold the reagents through releasable binding interactions as described above. In this embodiment, cleavage of a reagent in a specific spatial region can be carried out by applying cleavage conditions (such as applying light, temperature, electrical potential, etc.) in a manner that confines the cleavage condition to the specific spatial region of interest. In this embodiment, releasable binding interactions used for holding different reagents can be the same or different, because release of individual reagents can be directed by application of the cleavage condition to defined region. In a preferred embodiment, the device is configured for a multiplexed assay measurement and the device includes (a) a storage zone comprising a surface-reagent complex confined to the storage zone, the surface-reagent complex including (i) a reagent linked to a first targeting agent; and (ii) a surface linked to a second targeting agent, wherein the reagent and the surface are linked, in the surface-reagent complex, via a releasable binding interaction between the first and second targeting agents; and (b) a use zone comprising a plurality of assay regions configured to use the reagent in a multiplexed assay for a plurality of analytes in a sample. The storage zone may further comprise a second surface-reagent complex confined to the storage zone, the second surface-reagent complex including (iii) a second reagent linked to a third targeting agent; and (iv) a second surface linked to a fourth targeting agent, wherein the second reagent and the second surface are linked, in the second surface-reagent complex, via a second releasable binding interaction between the third and fourth targeting agents; and the use zone is ti further configured to use the second reagent in the multiplexed assay. In this regard, the use zone comprises two or more assay regions each configured to use the reagent and the second reagent in one or more assays conducted with the sample in the assay device, and this configuration of assay device enables the conduct of a plurality of assays in the use zone with the reagent and optionally, a second reagent. The use zone may include a first assay region configured to conduct an assay for a first analyte of interest in the sample and an additional assay region configured to conduct an assay for an additional analyte of interest in the sample, and an assay in such a device comprises the following steps:

(x) introducing the sample to the use zone via the storage zone;

(y) introducing a diluent to the storage zone;

(z) subjecting the storage zone to a condition that releases the reagent from the surface-reagent complex;

(xx) transferring the reagent from the storage zone to the first assay region and the second assay region; and (yy) conducting the assays in the first and second assay regions, respectively.

The conducting step of each assay may be performed simultaneously or sequentially.

Alternatively, an assay method may include an incubation step between the sample and free reagent before the mixture of sample and free reagent is introduced to the use zone: Such a method would include the following steps:

(x) introducing the sample to the storage zone;

(y) subjecting the storage zone to a condition that releases the reagent from the surface-reagent complex, and optionally incubated the sample with the free reagent in the storage zone;

(z) transferring the mixture formed in (y) from the storage zone to the first assay region and the second assay region; and (xx) conducting the assays in the first and second assay regions, respectively.

Still further, the use zone may include a first assay region configured to conduct an assay for a first analyte of interest in the sample and an additional assay region in the use zone configured to conduct an assay for an additional analyte of interest in the sample, and an assay in such a device may comprise:

(x) introducing the sample to the use zone via the storage zone;

(y) introducing a diluent to the storage zone and i) subjecting the storage zone to a condition that releases the reagent from the surface-reagent complex;

ii) subjecting the storage zone to an additional condition that releases a second reagent from a second surface-reagent complex;

(z) transferring the reagent and the second reagent from the storage zone to the first and second assay regions; and (xx) conducting the assays in the first and second assay regions.

The conducting step of each assay may be performed simultaneously or sequentially. Likewise, the transfer of the reagent and the second reagent may be done simultaneously or sequentially.

Alternatively, an assay method using a device that includes a first assay region configured to conduct an assay for a first analyte of interest in the sample and an additional assay region in the use zone configured to conduct an assay for an additional analyte of interest in the sample may also include an incubation step, i.e., (x) introducing the sample to the storage zone;

i) subjecting the storage zone to a condition that releases the reagent from the surface-reagent complex;

ii) subjecting the storage zone to an additional condition that releases a second reagent from a second surface-reagent complex;

(iii) incubating the storage zone with the free reagent and free second reagent formed in steps (x)(i) and (x)(ii);

(y) transferring the mixture formed in step (x)(iii) from the storage zone to the first and second assay regions; and (z) conducting the assays in the first and second assay regions.

In one specific embodiment, the assay device is a cartridge, such as that described in application Ser. No. 61/284,276, filed Dec. 16, 2009, the disclosure of which is incorporated herein by reference. As shown, e.g., in FIG. 9 of U.S. Ser. No. 61/284,276, a cartridge may include various compartments, i.e., a sample chamber, an assay reagent chamber, waste chambers, and detection chambers, as well as a fluidic network that connects various compartments and/or fluid ports/vents. The storage zone may be incorporated within, e.g., a reagent chamber, and likewise, the use zone may be included within, e.g., the detection chamber. Additionally or alternatively, an additional storage chamber may be incorporated within the cartridge described therein.

In another specific embodiment, the assay device is a multi-well assay plate, such as that described in co-pending application Ser. No. 11/642,970, filed Dec. 21, 2006, now U.S. Pat. No. 7,897,448, the disclosure of which is incorporated herein by reference. The assay plate may include a plate body with a plurality of wells defined therein, wherein the plurality of wells includes a binding surface having a capture reagent immobilized therein, and an additional reagent located on a surface of the plate or well that does not overlap with the binding surface. In one embodiment, the additional reagent is located on a reagent storage shelf positioned on a wall of a well. Alternatively, an assay plate may include assay wells that are connected to dedicated reagent spaces located in the regions between the assay wells. In such an embodiment, a reagent space may be in fluidic communication with the surrounding wells via e.g., a notch. In addition, suitable assay plates are described in U.S.

patent application Ser. No. 11/642,970, now U.S. Pat. No. 7,897,448, the disclosure of which is incorporated herein by reference.

(iii) Solid Phases

A wide variety of solid phases are suitable for use in the methods of the present invention including conventional solid phases from the art of binding assays. Solid phases may be made from a variety of different materials including polymers (e.g., polystyrene and polypropylene), ceramics, glass, composite materials (e.g., carbon-polymer composites such as carbon-based inks). Suitable solid phases include the surfaces of macroscopic objects such as an interior surface of an assay container (e.g., test tubes, cuvettes, flow cells, cartridges, wells in a multi-well plate, etc.), slides, assay chips (such as those used in gene or protein chip measurements), pins or probes, beads, ti filtration media, lateral flow media (for example, filtration membranes used in lateral flow test strips), etc.

Suitable solid phases also include particles (including but not limited to colloids or beads) commonly used in other types of particle-based assays e.g., magnetic, polypropylene, and latex particles, materials typically used in solid-phase synthesis e.g., polystyrene and polyacrylamide particles, and materials typically used in chromatographic applications e.g., silica, alumina, polyacrylamide, polystyrene. The materials may also be a fiber such as a carbon fibril. Microparticles may be inanimate or alternatively, may include animate biological entities such as cells, viruses, bacterium and the like.

The particles used in the present method may be comprised of any material suitable for attachment to one or more binding partners and/or labels, and that may be collected via, e.g., centrifugation, gravity, filtration or magnetic collection. A wide variety of different types of particles that may be attached to binding reagents are sold commercially for use in binding assays. These include non-magnetic particles as well as particles comprising magnetizable materials which allow the particles to be collected with a magnetic field. In one embodiment, the particles are comprised of a conductive and/or semiconductive material, e.g., colloidal gold particles.

The microparticles may have a wide variety of sizes and shapes. By way of example and not limitation, microparticles may be between 5 nanometers and 100 micrometers. Preferably microparticles have sizes between 20 nm and 10 micrometers. The particles may be spherical, oblong, rod-like, etc., or they may be irregular in shape.

The particles used in the present method may be coded to allow for the identification of specific particles or subpopulations of particles in a mixture of particles. The use of such coded particles has been used to enable multiplexing of assays employing particles as solid phase supports for binding assays. In one approach, particles are manufactured to include one or more fluorescent dyes and specific populations of particles are identified based on the intensity and/or relative intensity of fluorescence emissions at one or more wave lengths. This approach has been used in the Luminex xMAP systems (see, e.g., U.S. Pat. No. 6,939,720) and the Becton Dickinson Cytometric Bead Array systems. Alternatively, particles may be coded through differences in other physical properties such as size, shape, imbedded optical patterns and the like.

In certain embodiments of assays of the invention, particles may have a dual role as both i) a solid phase support used in an analyte concentration, collection and/or separation step and ii) as a detectable label or platform for detectable labels in a measurement step. In one example, a method of conducting a binding assay may comprise contacting a sample comprising an analyte with a particle linked to a first binding reagent that binds that analyte to form a complex comprising the analyte bound to the first binding reagent. The complex is then collected by collection of the particle (via magnetic collection, centrifugation, gravity sedimentation, etc.) and some or all of the unbound components of the sample are separated from the complex by removing some or all of the sample volume and, optionally, washing the collected particles. The complex is then released by resuspending the particles in the original or a new liquid media. The complex on the particle is then contacted with a second binding reagent bound to a solid phase, the second binding reagent binding the complex so as to bring the complex and particle to a surface of the solid phase. The amount of analyte in the sample is measured by measuring the amount of analyte bound to the solid phase, which in turn is measured by measuring the amount of particles bound to the solid phase (either by directly measuring the particles or by measuring detectable labels in or on the particles by, e.g., the measurement approaches described below).

The invention also includes assay methods that employ magnetic particles as detectable labels or as platforms for detectable labels in a binding assay. Advantageously, when using magnetic particles as a label or a label platform, a magnetic field can be applied to speed the kinetics for the binding of i) assay components linked to a magnetic particle to ii) binding reagents immobilized on a solid phase.

Accordingly, one embodiment is a method for conducting a binding assay comprising (a) contacting (i) a sample comprising a target analyte with (ii) a magnetic particle linked to a first binding reagent that binds the target analyte and thereby forms a complex comprising the target analyte bound to the first binding reagent;

(b) contacting a solution comprising the complex with a second binding reagent bound to a solid phase, wherein the second binding reagent binds to the complex;

(c) applying a magnetic field to concentrate the particles near to the solid phase and thereby accelerating the rate of binding between the complex and the second binding reagent and (d) measuring the amount of the analyte bound to the solid phase.

Optionally, such a method may also include, prior to step (b), collection and release steps as described elsewhere in this application so as to pre-concentrate the analyte and/or remove interferents from the sample. The magnetic particles used in such method are, preferably, between 10 nm and 10 um in diameter, more preferably between 50 nm and 1 um. The step of applying a magnetic field may be achieved through the use of permanent or electromagnets, e.g., by placing the magnet on the opposite side of the solid phase relative to the second binding reagent, Optionally, the magnet or magnetic field is translated and/or rotated along the solid phase so as to move the particles along the binding surface and allow the particles to interrogate the surface for available binding sites. Alternatively, or in conjunction with movement of the magnet/field, the magnetic field is intermittently removed and, while the magnetic field is removed, the particles are resuspended (e.g., by mixing) and then reconcentrated on the solid phase (thereby, allowing for allowing the particles to change rotational orientation on the surface and allowing them to interrogate additional areas on the surface. The method may also include a washing step, prior to the measuring step, to remove unbound particles.

During such a washing step, the magnetic field is removed to allow for non-bound particles to be washed away. Alternatively, a magnetic field above the surface can be used to pull unbound particles away from the surface. The magnetic reaction acceleration approach may also be applied to multiplexed assay methods, as described elsewhere in this application, e.g., the solid phase may include an array of a plurality of different second binding reagents for use in array-based multiplexed measurements.

(iv) Collection and Release

Collection, as used herein, refers to the physical localization of a material in a ti mixture. Collection includes the localization of a material through binding reactions or adsorption. For example, a material in a mixture may be collected on a solid phase by adsorption of the material on the solid phase or by binding of the material to binding reagents on the solid phase. Collection is not, however, limited to localization at a solid phase and may also include techniques in the art for localizing materials at a location/volume within a larger fluid volume, for example, localization of materials through the use of optical tweezers (which use light to manipulate microscopic objects as small as a single atom, wherein the radiation pressure from a focused laser beam is able to trap small particles), electric or magnetic fields, focused flow, density gradient centrifugation, etc.

Certain embodiments of the invention include the collection of microparticles or materials that are bound to microparticles. Suitable collection methods include the many methods known in the art of microparticle-based assays that achieve localization of microparticles from a suspension. These include sedimentation under gravity or by centrifugation, filtration onto a filter or porous membrane, localization (of magnetizable particles) by application of a magnetic field, binding or adsorption of the particles to a macroscopic solid phase, use of optical tweezers, etc.

Release, as used herein, refers to delocalization of a previously collected material. Materials that are held at a localized position through chemical bonds or through specific or non-specific binding interactions may be allowed to delocalize by breaking the bond or interaction so that the materials may diffuse or mix into the surrounding media. There are many well-established cleavable chemical linkers that may be used that provide a covalent bond that may be cleaved without requiring harsh conditions. For example, disulfide containing linkers may be cleaved using thiols or other reducing agents, cis-diol containing linkers may be cleaved using periodate, metal-ligand interactions (such as nickel-histidine) may be cleaved by changing pH or introducing competing ligands. Similarly, there are many well-established reversible binding pairs that may be employed (including those that have been identified in the art of affinity chromatography). By way of example, the binding of many antibody-ligand pairs can be reversed through changes in pH, addition of protein denaturants or chaotropic agents, addition of competing ti ligands, etc. Other suitable reversible binding pairs include complementary nucleic acid sequences, the hybridization of which may be reversed under a variety of conditions including changing pH, increasing salt concentration, increasing temperature above the melting temperature for the pair and/or adding nucleic acid denaturants (such as formamide). Such reversible binding pairs may be used as targeting agents (as described above), e.g., a first targeting agent may be linked to a first binding reagent that binds an analyte, a second targeting agent may be linked to a solid phase, and a binding interaction of the first and second targeting agents may be used to reversibly immobilize the first binding reagent on the solid phase.

Release also includes physical delocalization of materials by, for example, mixing, shaking, vortexing, convective fluid flow, mixing by application of magnetic, electrical or optical forces and the like. Where microparticles or materials bound to microparticles have been collected, such physical methods may be used to resuspend the particles in a surrounding matrix. Release may simply be the reverse of a previous collection step (e.g., by any of the mechanisms described above) or collection and release could proceed by two different mechanisms. In one such example, collection of materials (such as an analyte or a complex comprising an analyte) bound to a particle can be achieved by physical collection of the particle. The materials are then released by cleaving a bond or reversing a binding reaction holding the material on the particle. In a second such example, materials (such as an analyte of a complex comprising an analyte are collected on a surface through a binding interaction with a binding reagent that is linked to the surface. The material is then released by breaking a bond or a second binding interaction linking the binding reagent to the surface.

Collection followed by release may be used to concentrate and/or purify analytes in a sample. By collecting in a first volume and releasing into a second smaller volume, an analyte in a sample may be concentrated. Through concentration, it is often possible to significantly improve the sensitivity of a subsequent measurement step. By collecting from a sample and removing some or all of the uncollected sample, potential assay interferents in the sample may be reduced or eliminated. Optionally, removal of the unbound sample may include washing a collected material with and releasing the collected material into defined liquid reagents (e.g., assay or wash buffers) so as to provide a uniform matrix for subsequent assay steps.

(iv) Measurement Methods

The methods of the invention can be used with a variety of methods for measuring the amount of an analyte and, in particular, measuring the amount of an analyte bound to a solid phase. Techniques that may be used include, but are not limited to, techniques known in the art such as cell culture-based assays, binding assays (including agglutination tests, immunoassays, nucleic acid hybridization assays, etc.), enzymatic assays, colorometric assays, etc. Other suitable techniques will be readily apparent to one of average skill in the art. Some measurement techniques allow for measurements to be made by visual inspection, others may require or benefit from the use of an instrument to conduct the measurement.

Methods for measuring the amount of an analyte include label free techniques, which include but are not limited to i) techniques that measure changes in mass or refractive index at a surface after binding of an analyte to a surface (e.g., surface acoustic wave techniques, surface plasmon resonance sensors, ellipsometric techniques, etc.), ii) mass spectrometric techniques (including techniques like MALDI, SEMI, etc. that can measure analytes on a surface), iii) chromatographic or electrophoretic techniques, iv) fluorescence techniques (which may be based on the inherent fluorescence of an analyte), etc.

Methods for measuring the amount of an analyte also include techniques that measure analytes through the detection of labels which may be attached directly or indirectly (e.g., through the use of labeled binding partners of an analyte) to an analyte. Suitable labels include labels that can be directly visualized (e.g., particles that may be seen visually and labels that generate an measurable signal such as light scattering, optical absorbance, fluorescence, chemiluminescence, electrochemiluminescence, radioactivity, magnetic fields, etc). Labels that may be used also include enzymes or other chemically reactive species that have a chemical activity that leads to a measurable signal such as light scattering, absorbance, fluorescence, etc. The use of enzymes as labels has been well established in in Enzyme-Linked ImmunoSorbent Assays, also called ELISAs, Enzyme ImmunoAssays or EIAs. In the ELISA format, an unknown amount of antigen is affixed to a surface and then a specific antibody is washed over the surface so that it can bind to the antigen. This antibody is linked to an enzyme, and in the final step a substance is added that the enzyme converts to a product that provides a change in a detectable signal. The formation of product may be detectable, e.g., due a difference, relative to the substrate, in a measurable property such as absorbance, fluorescence, chemiluminescence, light scattering, etc. Certain (but not all) measurement methods that may be used with solid phase binding methods according to the invention may benefit from or require a wash step to remove unbound components (e.g., labels) from the solid phase. Accordingly, the methods of the invention may comprise such a wash step.

In one embodiment, an analyte(s) of interest in the sample may be measured using electrochemiluminescence-based assay formats, e.g. electrochemiluminescence (ECL) based immunoassays. The high sensitivity, broad dynamic range and selectivity of ECL are important factors for medical diagnostics. Commercially available ECL instruments have demonstrated exceptional performance and they have become widely used for reasons including their excellent sensitivity, dynamic range, precision, and tolerance of complex sample matrices. Species that can be induced to emit ECL (ECL-active species) have been used as ECL, labels, e.g., i) organometallic compounds where the metal is from, for example, the noble metals of group VIII, including Ru-containing and Os-containing organometallic compounds such as the tris-bipyridyl-ruthenium (RuBpy) moiety and ii) luminol and related compounds. Species that participate with the ECL label in the ECL process are referred to herein as ECL coreactants. Commonly used coreactants include tertiary amines (e.g., see U.S. Pat. No. 5,846,485), oxalate, and persulfate for ECL from RuBpy and hydrogen peroxide for ECL from luminol (see, e.g., U.S. Pat. No. 5,240,863). The light generated by ECL labels can be used as a reporter signal in diagnostic procedures (Bard et al., U.S. Pat. No. 5,238,808, herein incorporated by reference). For instance, an ECL label can be covalently coupled to a binding agent such as an antibody, nucleic acid probe, receptor or ligand; the participation of the binding reagent in a binding interaction can be monitored by ti measuring ECL, emitted from the ECL label. Alternatively, the ECL signal from an ECL-active compound may be indicative of the chemical environment (see, e.g., U.S. Pat. No. 5,641,623 which describes ECL assays that monitor the formation or destruction of ECL coreactants). For more background on ECL, ECL labels, ECL assays and instrumentation for conducting ECL assays see U.S. Pat. Nos. 5,093,268; 5,147, 806; 5,324,457; 5,591,581; 5,597,910; 5,641,623; 5,643, 713; 5,679,519; 5,705,402; 5,846,485; 5,866,434; 5,786, 141; 5,731,147; 6,066,448; 6,136,268; 5,776,672; 5,308, 754; 5,240,863; 6,207,369; 6,214,552 and 5,589,136 and Published PCT Nos. WO 99/63347; WO 00/03233; WO 99/58962; WO 99/32662; WO 99/14599; WO 98/12539; WO 97/36931 and WO 98/57154, all of which are incorporated herein by reference.

The capture/collection and release methods of the invention may be applied to singleplex or multiplex formats where multiple assay measurements are performed on a single sample. Multiplex measurements that can be used with the invention include, but are not limited to, multiplex measurements i) that involve the use of multiple sensors; ii) that use discrete assay domains on a surface (e.g., an array) that are distinguishable based on location on the surface; iii) that involve the use of reagents coated on particles that are distinguishable based on a particle property such as size, shape, color, etc.; iv) that produce assay signals that are distinguishable based on optical properties (e.g., absorbance or emission spectrum) or v) that are based on temporal properties of assay signal (e.g., time, frequency or phase of a signal).

(v) Assay Formats

One embodiment of the present invention employs a specific binding assay, e.g., an immunoassay, immunochromatographic assay or other assay that uses a binding reagent. The immunoassay or specific binding assay according to one embodiment of the invention can involve a number of formats available in the art. The antibodies and/or specific binding partners can be labeled with a label or immobilized on a surface. Thus, in one embodiment, the detection method is a binding assay, e.g., an immunoassay, receptor-ligand binding assay or hybridization assay, and the detection is performed by contacting an assay composition with one or more detection molecules capable of specifically binding with an analyte(s) of interest in the sample.

In one embodiment, the assay uses a direct binding assay format. An analyte is bound to a binding partner of the analyte, which may be immobilized on a solid phase. The bound analyte is measured by direct detection of the analyte or through a label attached to the analyte (e.g., by the measurements described above).

In one embodiment, the assay uses a sandwich or competitive binding assay format. Examples of sandwich immunoassays performed on test strips are described in U.S. Pat. No. 4,168,146 to Grubb et al. and U.S. Pat. No. 4,366,241 to Tom et al., both of which are incorporated herein by reference. Examples of competitive immunoassay devices suitable for use with the present methods include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

Figure 1B:
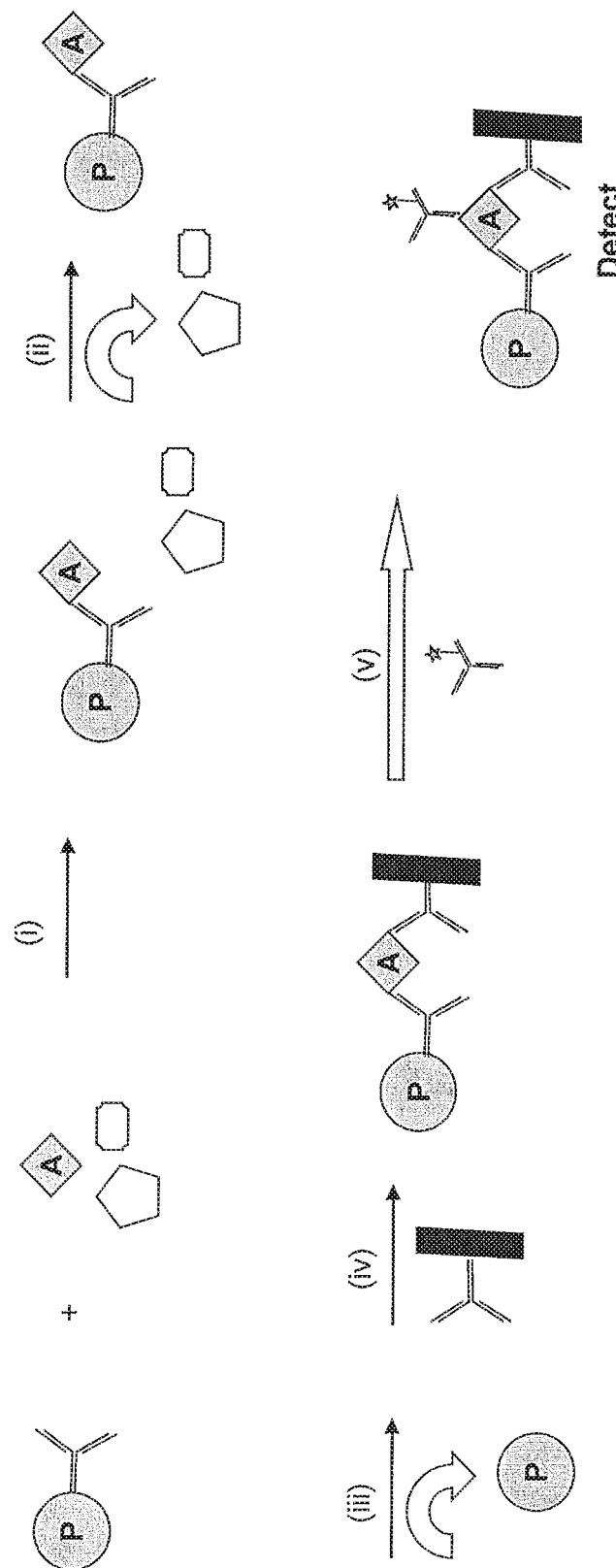

In a sandwich assay, analyte in the sample is bound to a first binding reagent and a second labeled binding reagent and the formation of this "sandwich" complex is measured. In a solid phase sandwich assay, the first binding reagent is immobilized on a solid phase and the amount of labeled antibody on the solid phase, due to formation of the sandwich complex, is then measured. The signal generated in a sandwich assay will generally have a positive correlation with the concentration of the analyte. Various configurations of sandwich assays that use the methods of the present invention are shown in FIGS. 1-4. In one embodiment, e.g., in FIG. 1(a), the assay includes contacting a sample comprising a target analyte with a particle or solid phase linked to a first binding reagent that binds the target analyte, thereby forming a complex comprising the target analyte bound to the first binding reagent. The complex is collected, separated and released, as described herein, and then a sandwich is formed by contacting the complex with an additional binding reagent (e.g., a second binding reagent). As shown in FIG. 1(a) and FIG. 1(b), the particle or solid phase may or may not be cleaved from the complex prior to contacting the complex with an additional binding reagent.

Figure 6A:
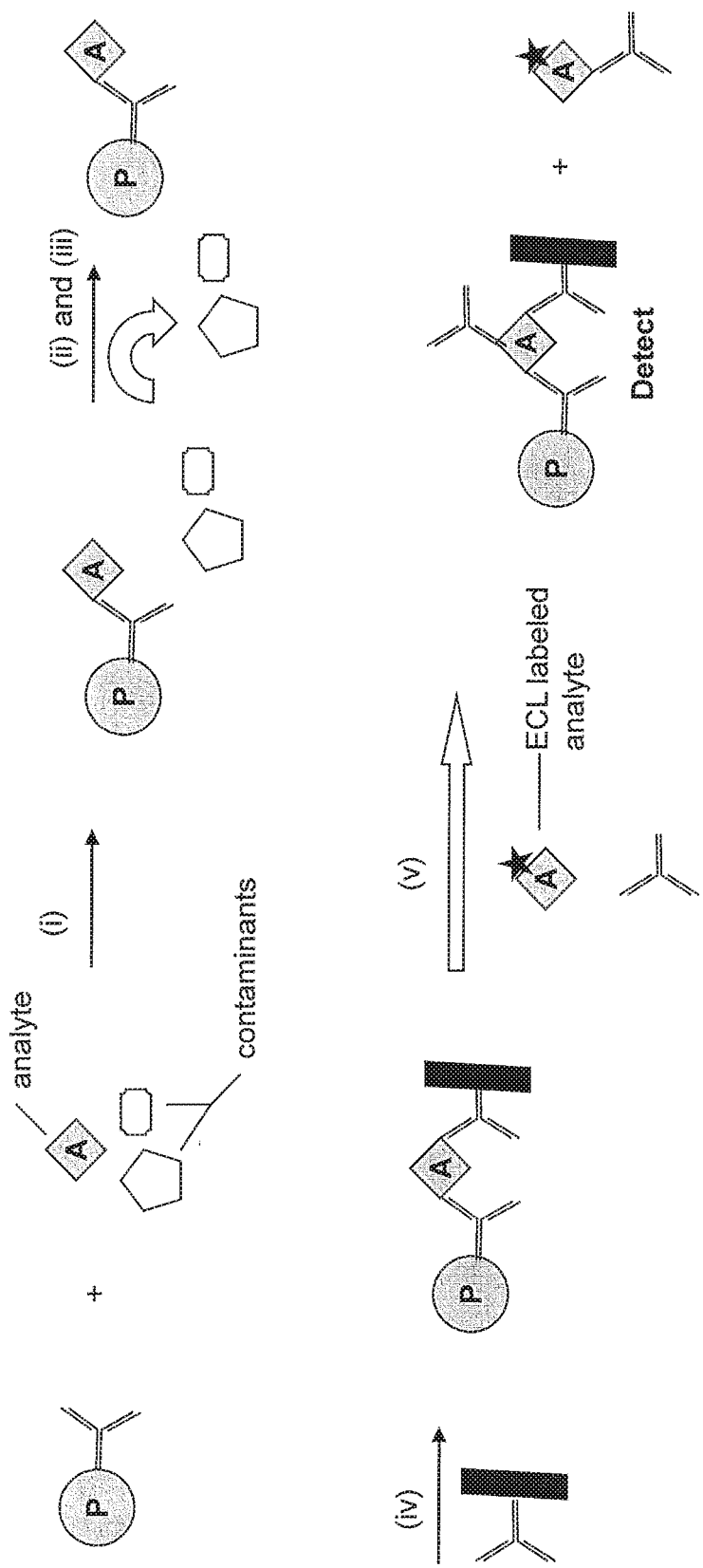
FIGS. 6(a)-6(b) illustrate two alternative competitive immunoassays according to the methods of the present invention.
Figure 6B:
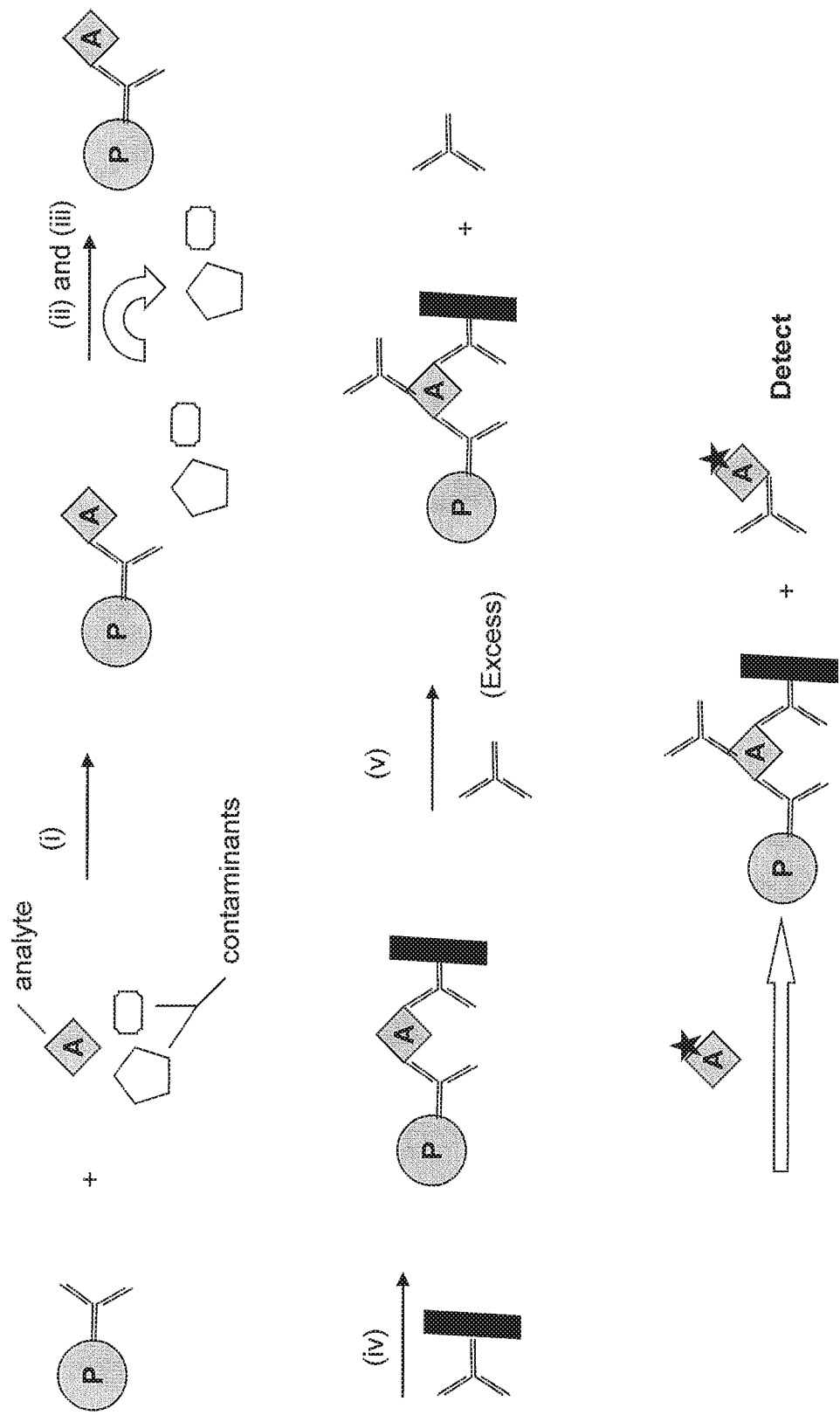

In a competitive assay, unlabelled analyte in the test sample is measured by its ability to compete with labeled or immobilized analyte. In the example of competitive assays employing labeled analytes, the unlabeled analyte in a sample blocks the ability of the labeled analyte to bind a binding reagent by occupying the binding site. Thus, in a competitive assay, the signal generated has an inverse correlation with the concentration of analyte in a sample. FIGS. 6(a) and 6(b) show the use of the methods of the present invention in a two step competitive format. As in FIG. 1(a), the analyte of interest in the sample is pre-concentrated. Labeled analyte bound to a solid support is incubated with the pre-concentrated analyte complex. FIGS. 6(a) and 6(b) serve to illustrate how the methods of the present invention may be used in a competitive assay format. The skilled artisan will understand that alternate configurations of a competitive immunoassay may be achieved using the methods of the present invention without undue experimentation.

(vi) Specific Embodiments

In one embodiment, a method is provided for conducting a binding assay comprising contacting a sample comprising a target analyte, A, and which may also contain various sample contaminants as shown in FIG. 1(a), with a particle linked to a first binding reagent that binds the target analyte and thereby forms a complex comprising the target analyte bound to the first binding reagent. Once the sample is mixed with the particle to form the complex, the complex is collected. This collection step may involve accumulation of the complex at a surface, e.g., by centrifugation of the particles, allowing the particles to rise or settle under gravity, filtering the particles onto a filtration media, magnetically collecting the particles (in the case of magnetic particles), etc. Alternatively, the collection step may involve accumulation of the complex within a defined volume within the sample, e.g., by holding the particles in this defined volume through the use of optical tweezers or focused flow. Optionally, the unbound components of the sample are then separated from the complex, e.g., by removing all or part of the non-collected components and/or by washing the collected complex with an additional assay medium or wash buffer. Thereafter, the complex is released, e.g., resuspended into the assay medium, and the complex is contacted with a second binding reagent bound to a solid phase, wherein the second binding reagent binds to the complex. The amount of analyte is detected by measuring the amount of a detectable label linked to an assay component bound to the solid phase. The detectable label may be linked to the first binding reagent, an optional third binding reagent, if one is used in the assay format, the particle or an additional assay component that is comprised within or bound to the complex.

Figure 1C:
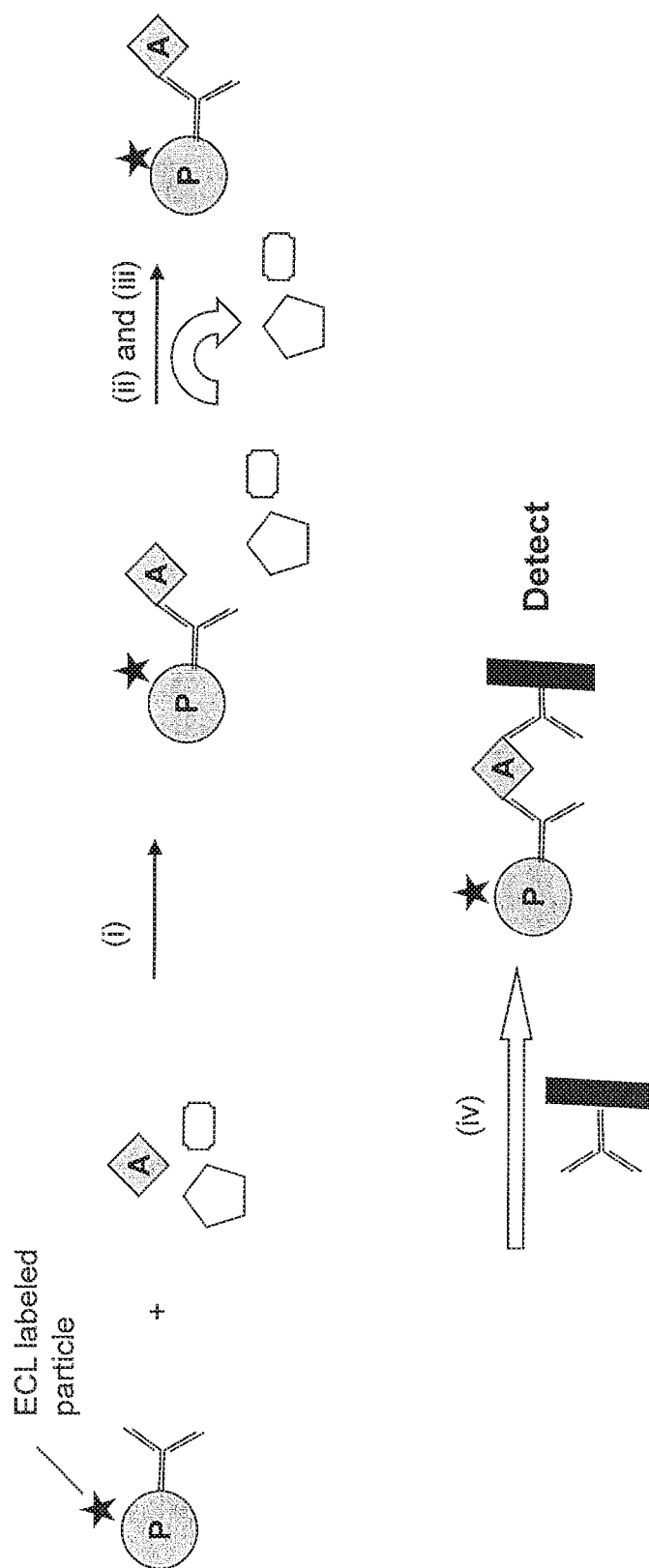
Figure 1D:
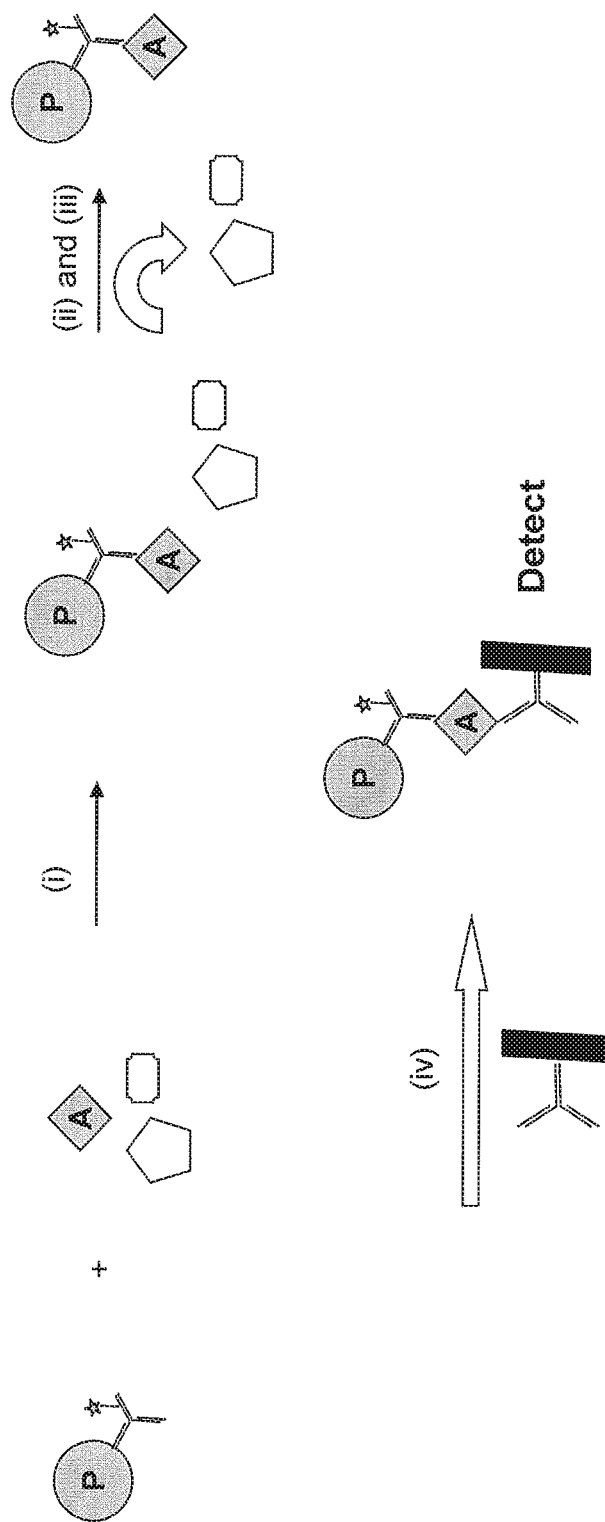
Figure 1E:
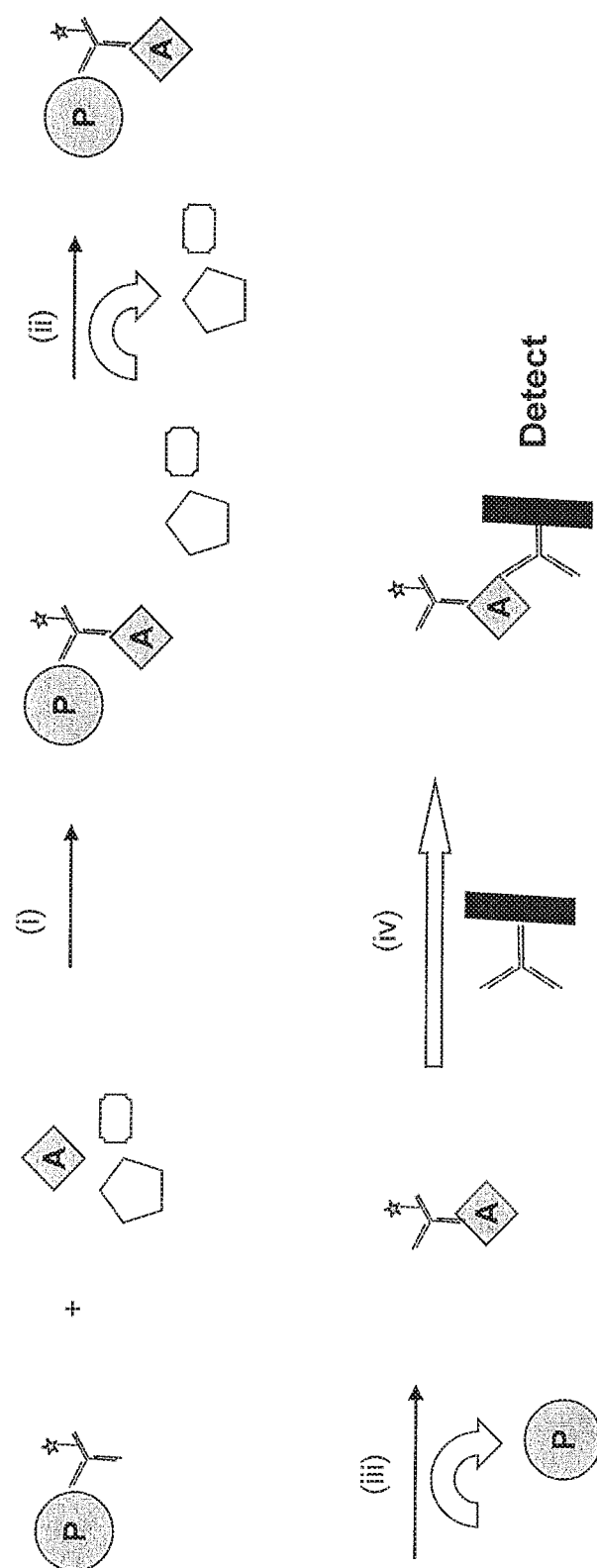

A variety of approaches are provided for conducting the collection and release steps described above and for providing the labeled reagent. FIG. 1(a) shows a method with the following steps: (i) a first binding reagent linked to a particle binds to the analyte to form a complex, (ii and iii) the complex is collected and released by collection and resuspension of the particle during which steps the analyte may be concentrated and/or separated from contaminants in the sample, (iv) the complex binds to a second binding reagent on a solid phase and (v) the complex is contacted with a labeled third binding reagent that binds the analyte in the complex such that it can be detected. FIG. 1(b) shows a method similar to the one in FIG. 1(a), except that the complex is released in step (iii) by cleaving the first binding reagent from the particle instead of simply resuspending the particle. FIGS. 1(c) and 1(d) show methods similar to the one in FIG. 1(a) except that that the label is attached to (or incorporated within) the particle (FIG. 1(c)) or attached to the first binding reagent (FIG. 1(d)) and the step of contacted the complex with a labeled third binding reagent is omitted. Alternatively, if the particle is measured directly (e.g., by direct visual observation of the particle), the label may be omitted. FIG. 1(e) shows a method similar to the one in FIG. 1(b) except that the label is attached to the first binding reagent and the step of contacting the complex with a labeled third binding reagent is omitted.

The measuring step may comprise any suitable method of measuring the presence of a detectable label in a sample (see the Measurement Methods section), e.g., optical absorbance, fluorescence, phosphorescence, chemiluminescence, light scattering or magnetism. In one embodiment, the detectable label is an electrochemiluminescent label and the measuring step comprises measuring an ECL signal and correlating that signal with an amount of analyte in the sample. Thus, the measuring step may further comprise contacting the complex with an electrode and applying a voltage waveform to the electrode to generate ECL.

The methods described in FIGS. 1(a)-1(e) may be applied to multiplex measurements for multiple analytes in a sample. In such methods, the first, second and ti third binding reagents (if present) may be selected to bind multiple analytes (e.g., the use of poly-dT as a binding reagent to capture multiple mRNAs in a sample through the common poly-dA tail sequence) or, alternatively, the methods may employ a plurality of different first binding reagents, second binding reagents and/or third binding reagents to bind to the multiple analytes. To allow for independent measurement of different analytes, such multiplex methods employs at least one of the group consisting of i) a plurality of different first binding reagents, ii) a plurality of second binding reagents and iii) a plurality of third binding reagents (the different reagents within (i), (ii) or (iii) being selected for their ability to preferentially bind a target analyte relative to other target analytes). Where a plurality of first binding reagents are used, individual particles may be attached to mixtures of the different first binding reagents or, alternatively, the particles may be prepared so that individual particles are attached to only one type of first binding reagent (e.g., such that an individual particle preferentially binds one of the target analytes relative to other target analytes).

The multiplex methods may use a variety of approaches for independently measuring different analytes. In one embodiment, a plurality of labeled binding reagents with different preferences for target analytes may be used (e.g., a plurality of different labeled third binding reagents as in FIGS. 1(a) and 1(b), a plurality of different labeled first binding reagents as in FIG. 1(e) or a plurality of different labeled first binding reagent-particle conjugates as in FIGS. 1(c) and 1(d)). The labels on the different labeled reagents (or, alternatively, the particles in the particle conjugates) are selected to provide distinguishable assay signals such that the different labeled reagents and, therefore, the different target analytes, can be measured independently. In another embodiment, a plurality of second binding reagents with different preferences for target analytes may be used. The different second binding reagents may be patterned into different discrete binding domains on one or more solid phases (e.g., as in a binding array) such that assay signals generated on the different binding domains and, therefore, the different analytes, can be measured independently (e.g., by independently addressing binding domains on electrode arrays or by independently measuring light emitted from different binding domains in a luminescence assay). Alternatively, the different second binding reagents ti may be coupled to different coded beads (as described in the Solid Phases section) to allow for the different analytes to be measured independently.

Figure 2A:
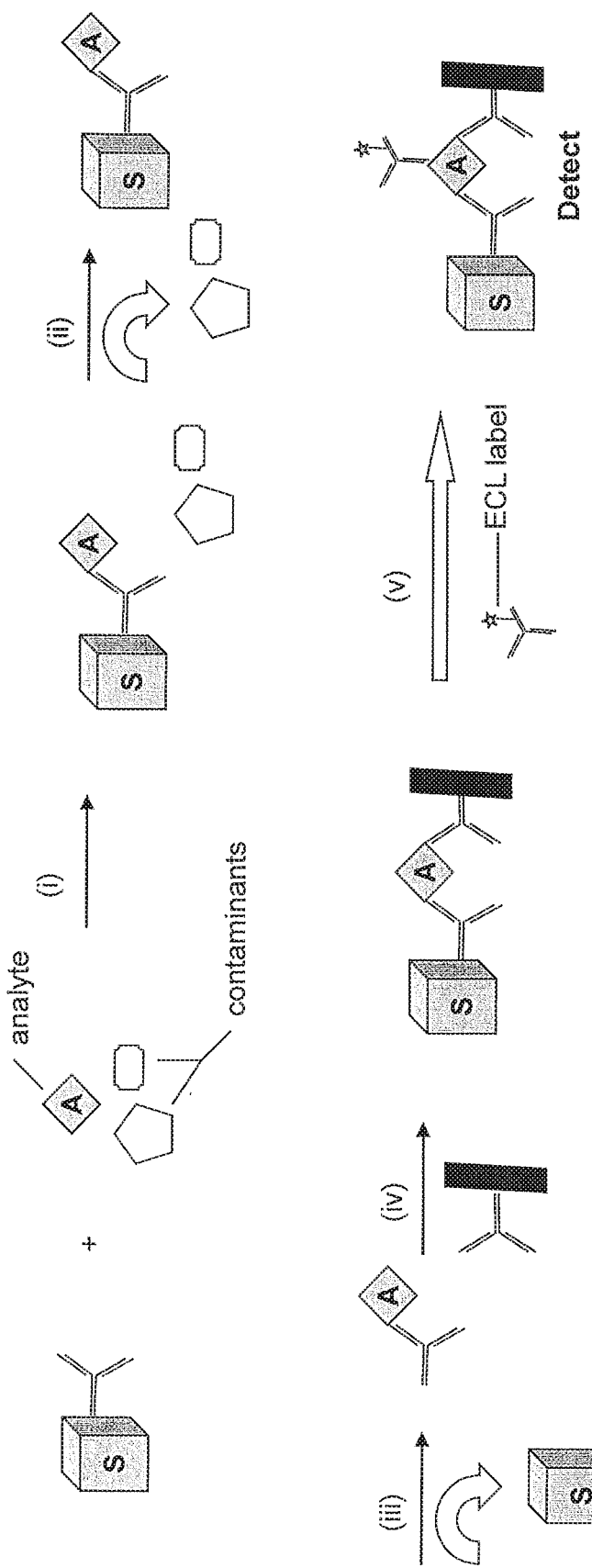
FIGS. 2(a)-2(b) illustrate various assay formats in which a first solid phase is used as an assay component.
Figure 2B:
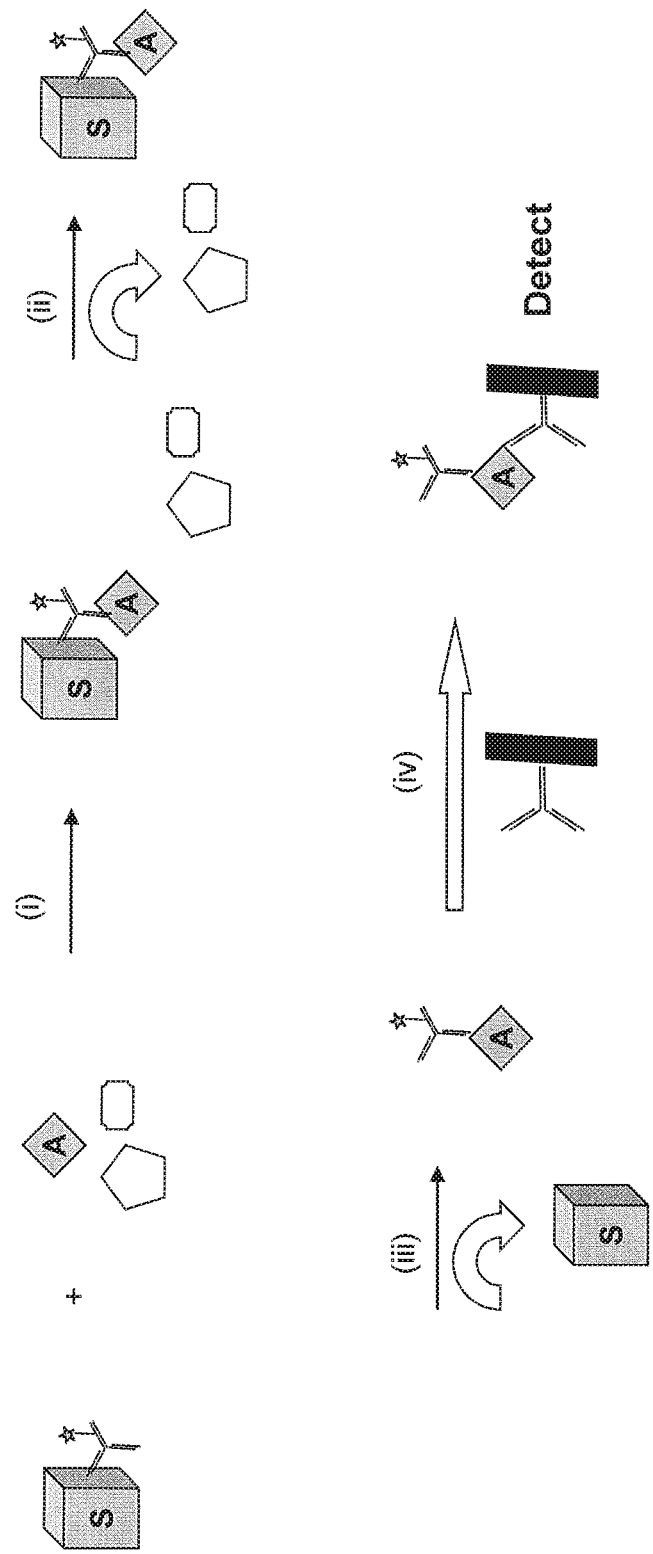

In an alternative embodiment, a method of conducting a binding assay is provided as shown in FIGS. 2(a)-2(b), which comprises contacting a sample comprising a target analyte with a first solid phase, S, linked to a first binding reagent that binds the target analyte and forms a complex comprising the target analyte bound to the first binding reagent. Once the sample is contacted with the first solid phase, the unbound components of the sample are separated from the complex, the complex is released from the solid phase into the assay medium and the first solid phase is removed from the first binding reagent. Thereafter, the released complex is contacted with a second solid phase comprising a second binding reagent that binds to the complex, and the amount of analyte bound to the second solid phase is quantified. The detectable label may be linked to the first binding reagent, an optional third binding reagent, if one is used in the assay format, the particle or an additional assay component that is comprised within or bound to the complex. In FIG. 2(a), the label is attached to a third binding reagent (and the method includes the step of contacting the complex with the third binding reagent), whereas the label is attached to the first binding reagent in FIG. 2(b).

As described for FIG. 1, the methods described in FIG. 2 may also be extended to multiplex measurements, e.g., by employing at least one of the group consisting of i) a plurality of different first binding reagents, ii) a plurality of second binding reagents and iii) a plurality of third binding reagents (the different reagents within (i), (ii) or (iii) being selected for their ability to preferentially bind a target analyte relative to other target analytes).

The invention also provides a method of conducting a multiplexed binding assay for a plurality of analytes that includes contacting (i) a sample with (ii) one or more first solid phases linked to one or more first binding reagents that bind the analytes to form complexes comprising the analytes bound to the first binding reagents. The unbound components of the sample are, optionally, separated from the complexes. The complexes are released and then contacted with a plurality of binding domains comprising second binding reagents that bind to the complexes, wherein each binding domain comprises a second binding reagent that binds to a complex comprising a secondary target analyte. Thereafter, the amount of analyte bound to the binding domains is measured.

According to another embodiment, a multiplexed assay may comprise the acts of contacting at least a portion of a sample with one or more binding surfaces comprising a plurality of binding domains, immobilizing one or more analytes on the domains and measuring the analytes immobilized on the domains. In certain embodiments, at least two of the binding domains differ in their specificity for analytes of interest. In one example of such an embodiment, the binding domains are prepared by immobilizing, on one or more surfaces, discrete domains of binding reagents that bind analytes of interest. Optionally, the sample is exposed to a binding surface that comprises an array of binding reagents. Optionally, the surface(s) may define, in part, one or more boundaries of a container (e.g., a flow cell, well, cuvette, etc.) which holds the sample or through which the sample is passed. The method may also comprise generating assay signals that are indicative of the amount of the analytes in the different binding domains, e.g., changes in optical absorbance, changes in fluorescence, the generation of chemiluminescence or electrochemiluminescence, changes in reflectivity, refractive index or light scattering, the accumulation or release of detectable labels from the domains, oxidation or reduction or redox species, electrical currents or potentials, changes in magnetic fields, etc.

Assays of certain embodiments of the invention may employ targeting agents to link the target analyte with a binding reagent in the assay medium. Such assay formats are illustrated in FIGS. 3(a)-3(e) and FIGS. 4(a)-4(b), which are analogous to FIGS. 1(a)-1(e) and FIGS. 2(a)-2(b), except that the binding of analyte to a first binding reagent on a solid phase/particle takes place through two steps: (i(a)) contacting the first binding reagent linked to a first targeting agent to a particle (or other solid phase) linked to a second targeting agent that binds to the first targeting agent (thus attaching the first binding reagent to the particle or other solid phase) and (i(h)) contacting the first binding reagent with a sample comprising a target analyte that binds the first binding reagent. Step i(a) may occur before step i(b) (as shown in the figures) or the two steps may occur in the reverse order or concurrently. Steps i(a) and i(b) may both be carried out during the conduct of an assay or, alternatively, the first binding reagent may be supplied to the user ti pre-bound to the solid phase through the targeting agents (e.g., if the targeting agents were pre-bound during manufacturing), in which case step i(a) may be omitted.

Figure 3A:
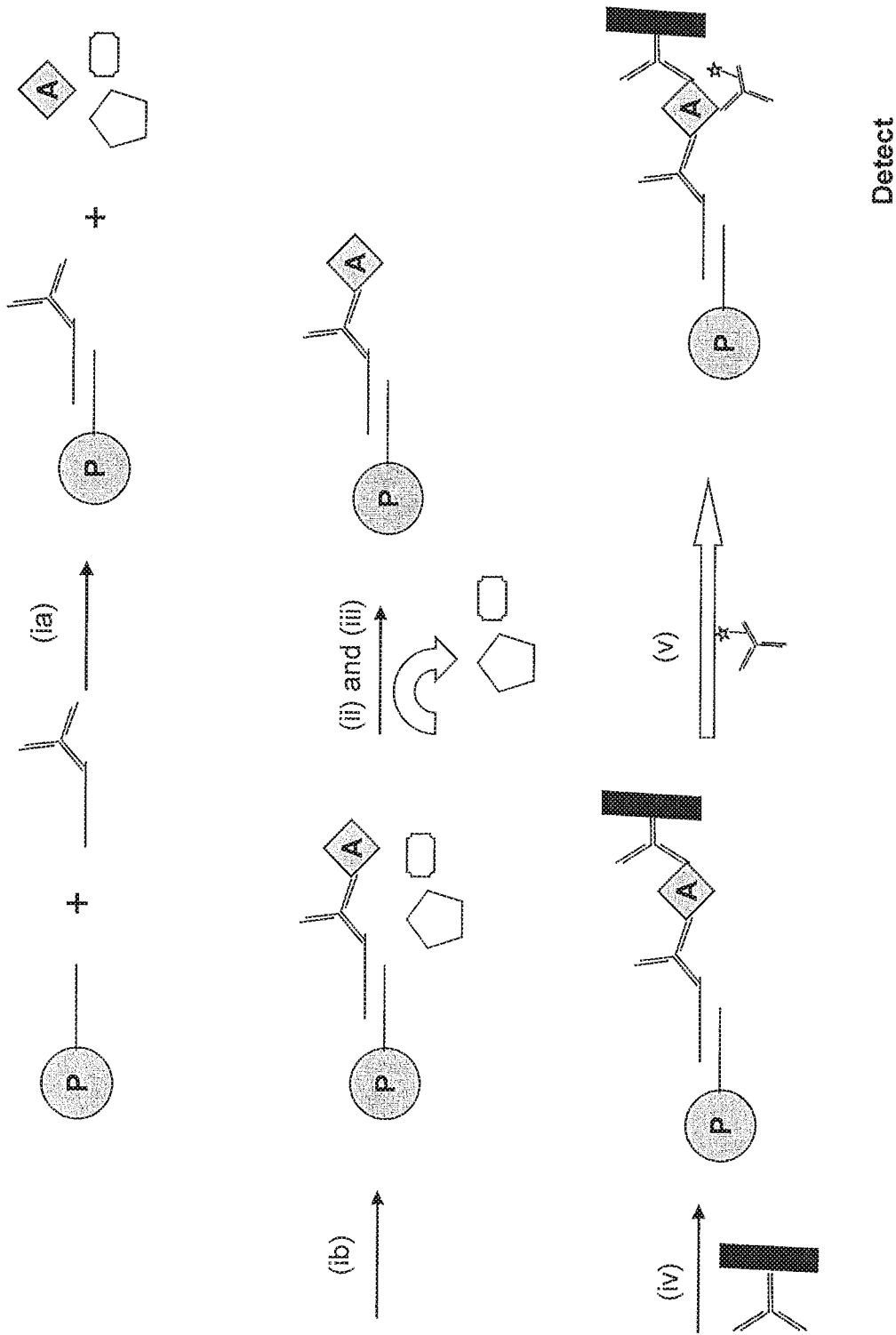
FIGS. 3(a)-3(e) illustrate various assay formats in which a particle is used as an assay component, to which a targeting agent is linked.
Figure 3B:
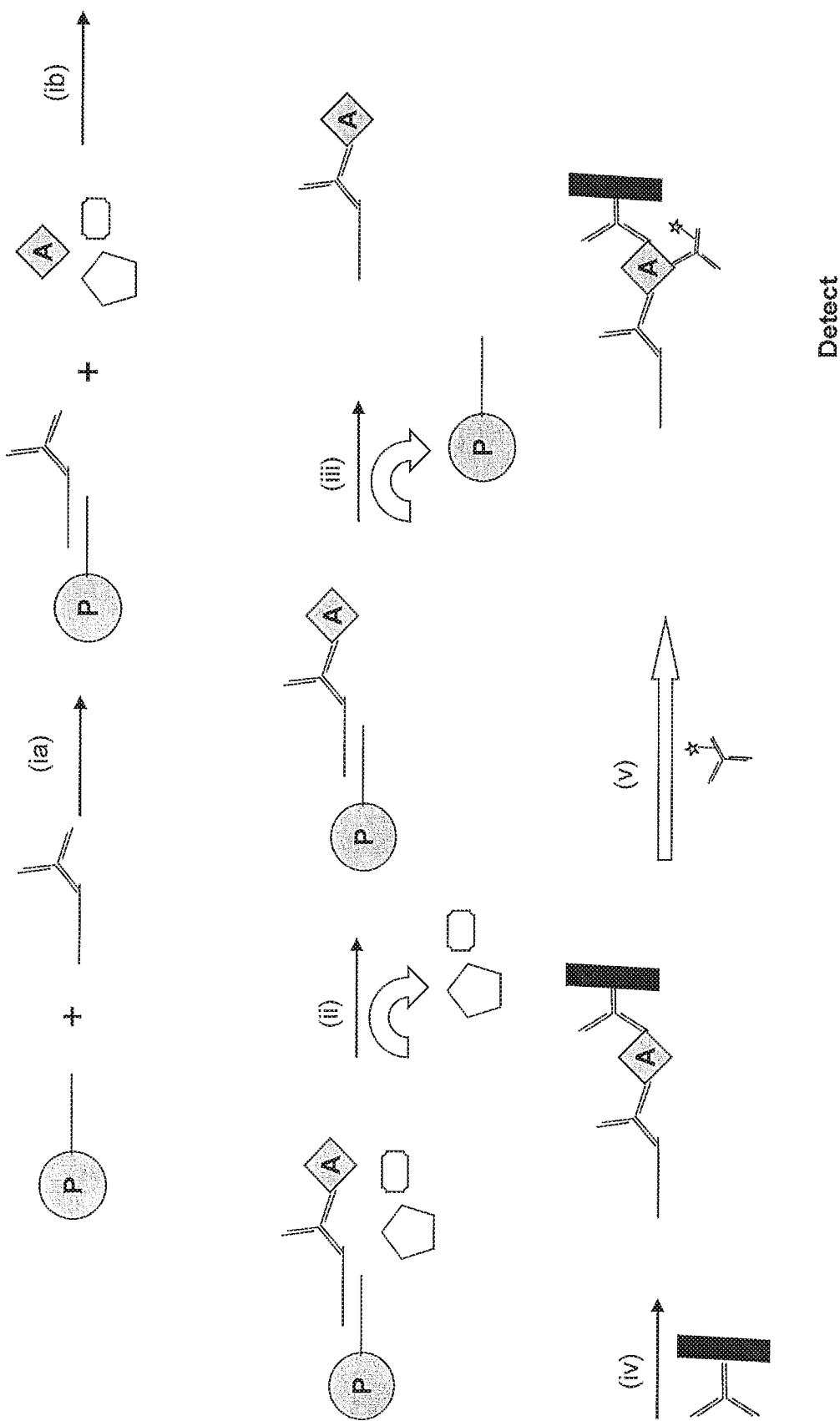
Figure 3C:
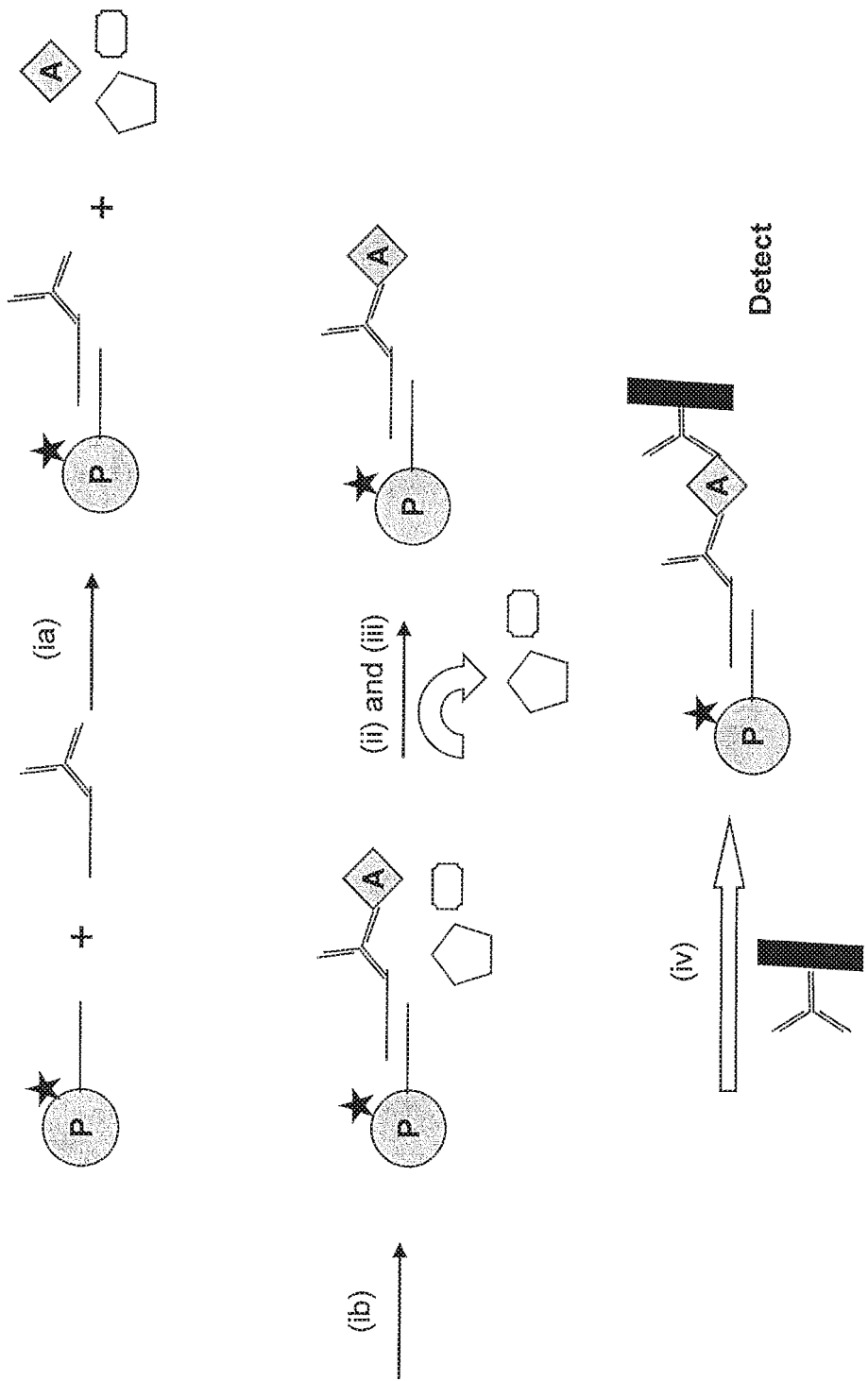
Figure 3D:
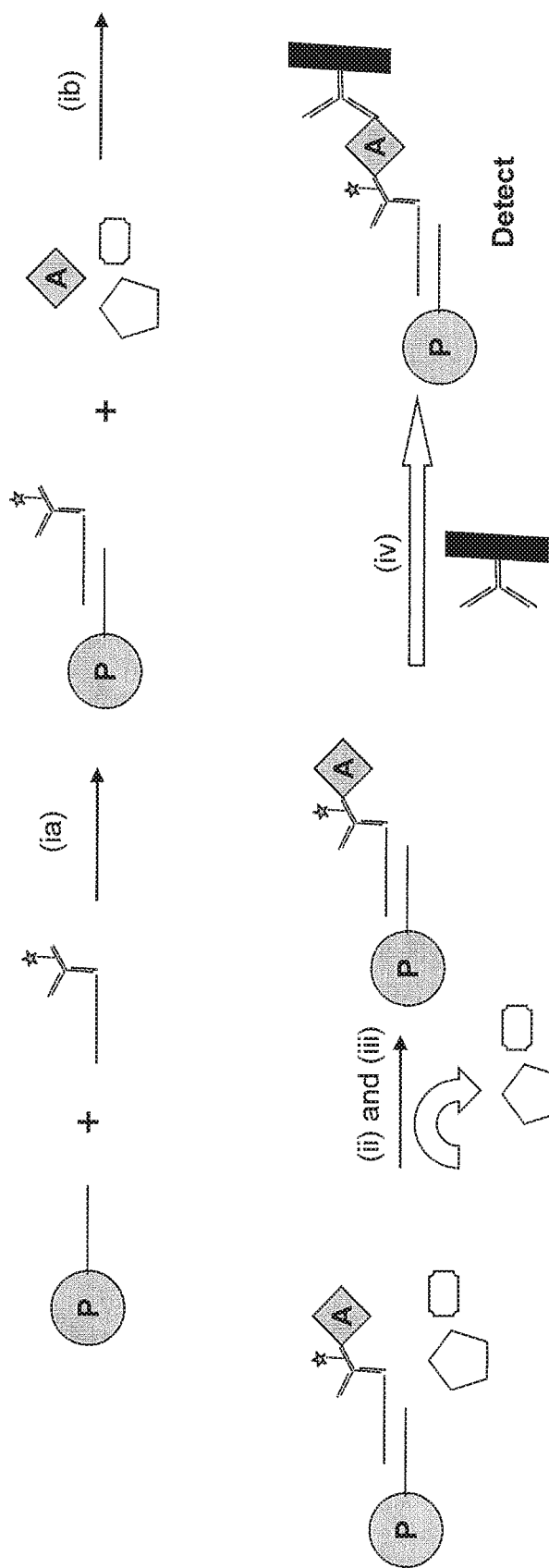
Figure 3E:
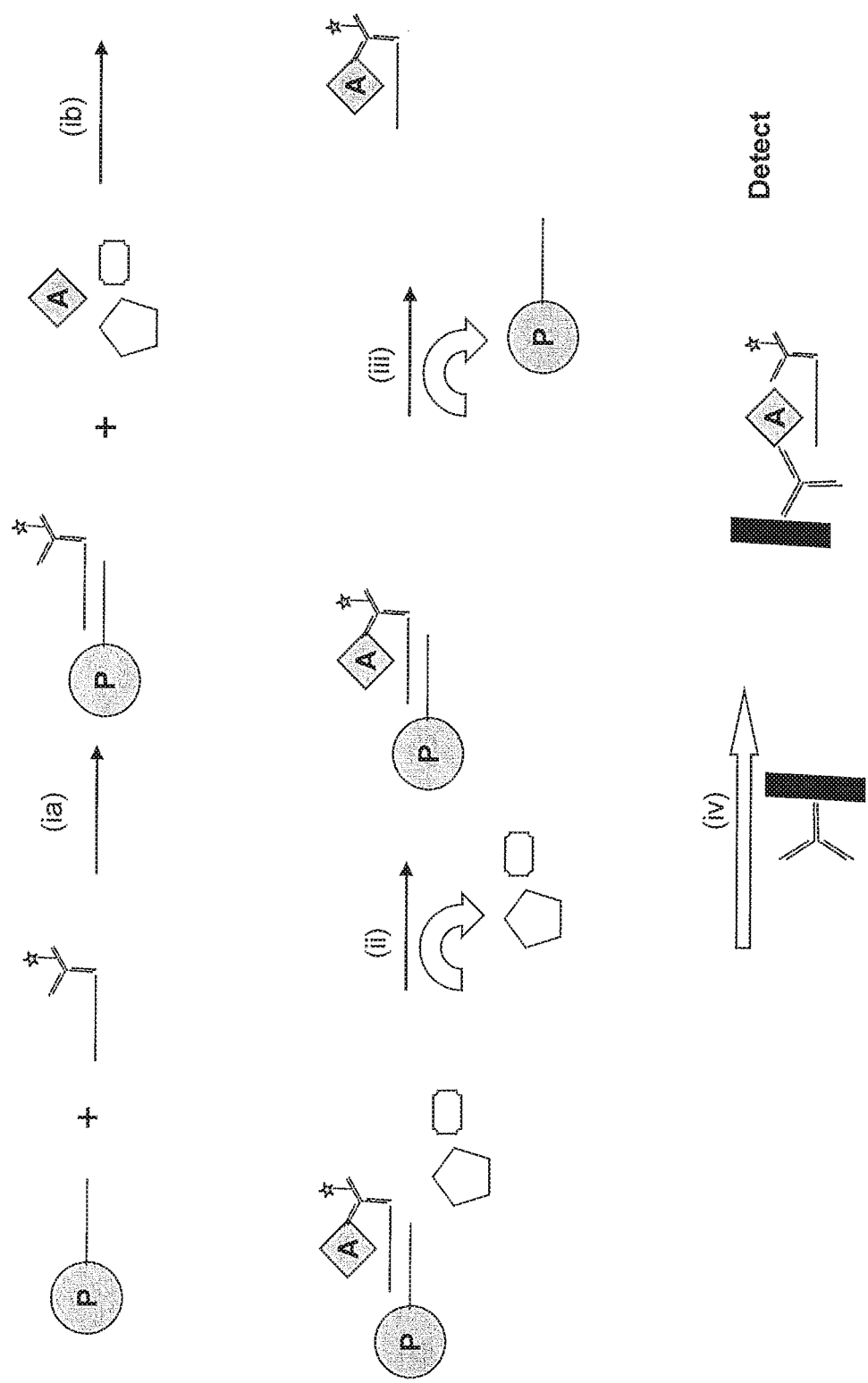

Thus, in one embodiment, the method includes contacting a sample comprising a target analyte with a particle linked to a first binding reagent that binds the target analyte, wherein the first binding reagent is linked to a first targeting agent and the particle is linked to a second targeting agent, and the first binding reagent and the particle are linked via a binding reaction between the first and second targeting agents to form a complex comprising the target analyte bound to the first binding reagent (see e.g., FIG. 3(a)). The complex is then collected and unbound components in the sample are separated from the complex. The complex is released and the released complex is contacted with a second binding reagent bound to a solid phase, wherein the second binding reagent binds to the complex. The amount of analyte bound to the solid phase is measured. As in the embodiments described above and illustrated in FIGS. 1(a)-1(e), the detectable label may be attached to various assay components in the medium, e.g., to a third binding reagent, as in FIGS. 3(a)-3(b), to the particle, as in FIG. 3(c), or to the first binding reagent, as in FIGS. 3(d)-3(e). Moreover, the complex is optionally cleaved from the particle prior to the detection step, as in FIGS. 3(b) and 3(d).

Figure 4A:
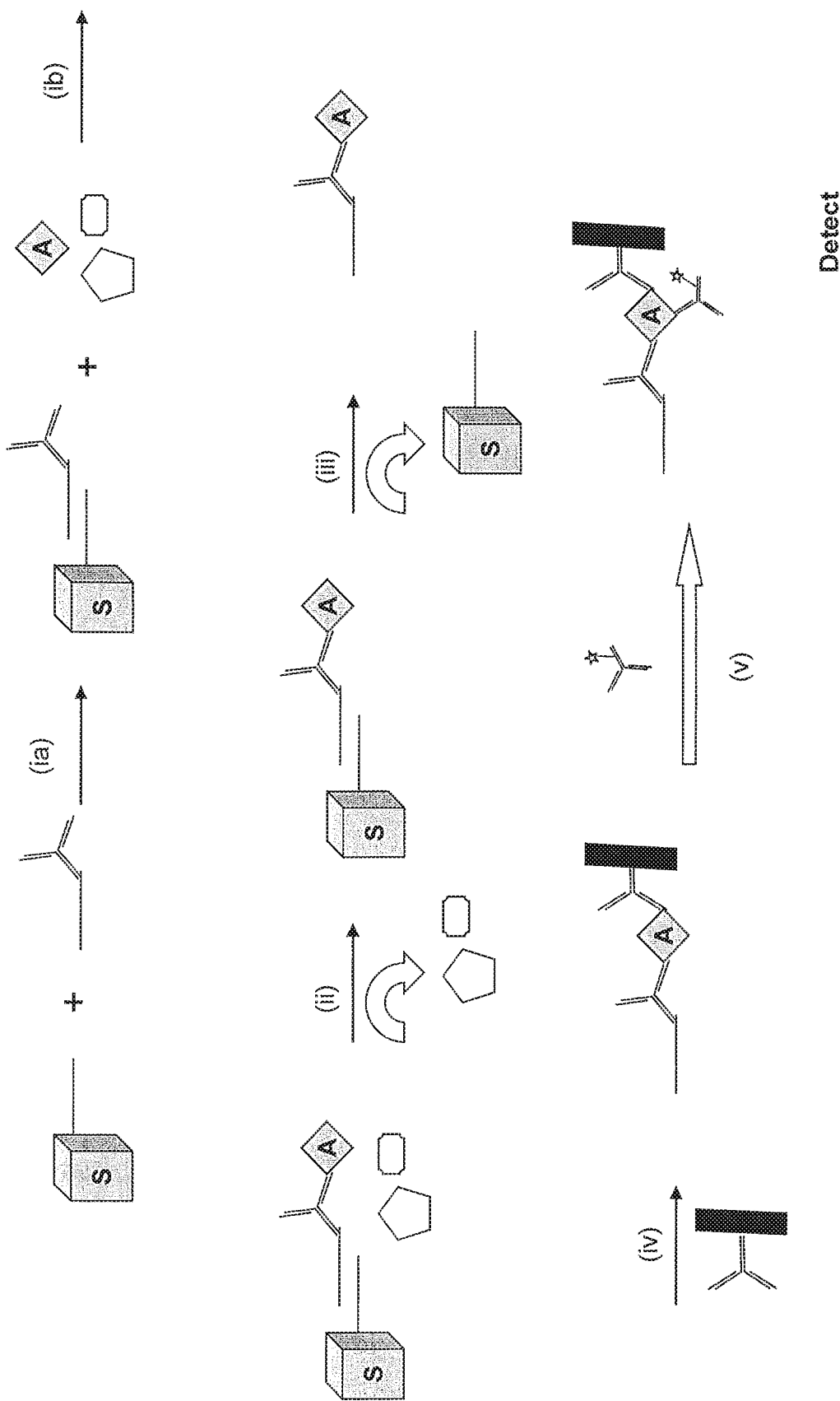
FIGS. 4(a)-4(b) illustrate various assay formats in which a first solid phase is used as an assay component, to which a targeting agent is linked.
Figure 4B:
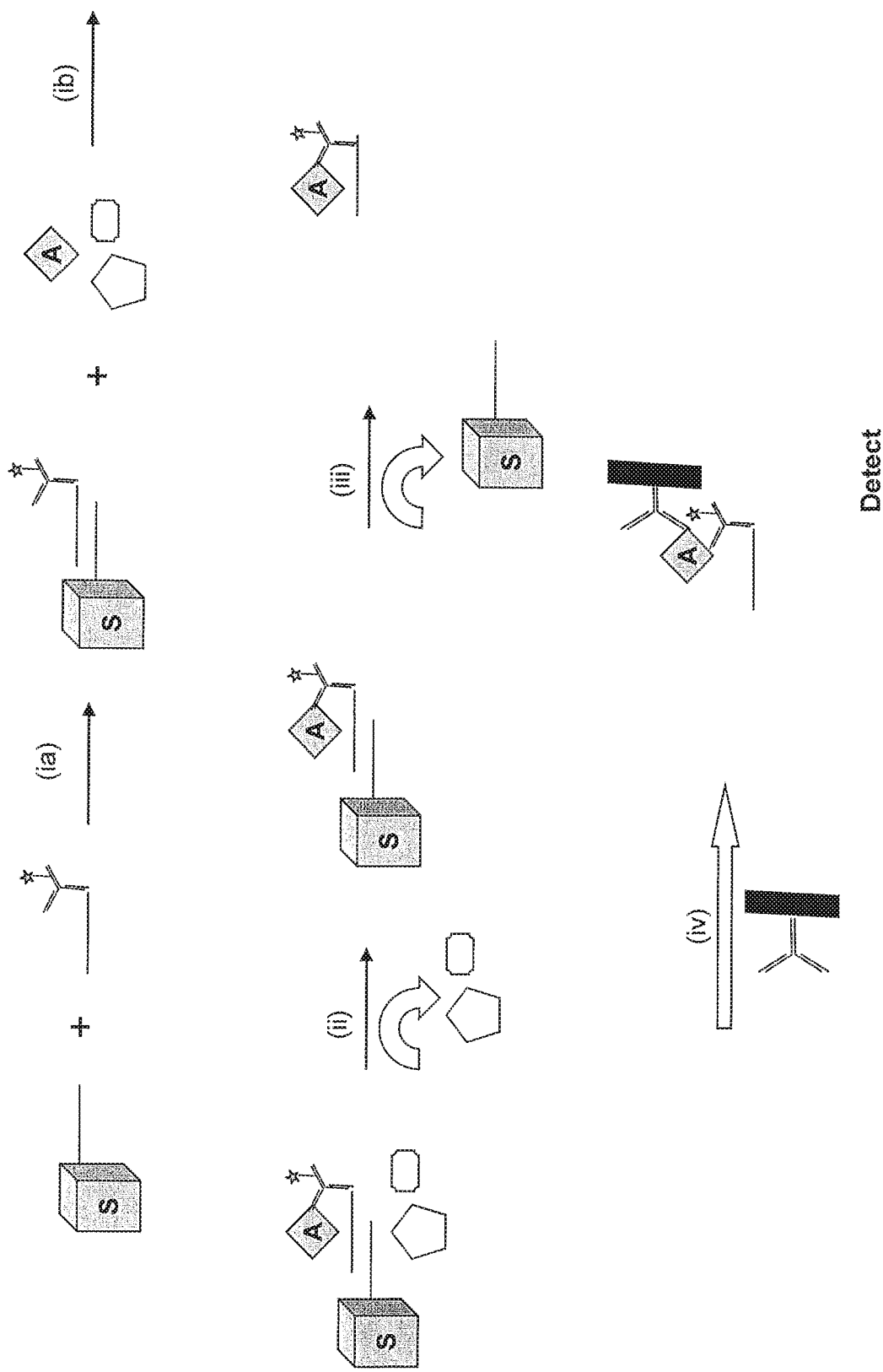

In one embodiment, the assay may include (a) contacting a sample comprising a target analyte with a first solid phase linked to a first binding reagent that binds the target analyte, wherein the first binding reagent is linked to a first targeting agent and the first solid phase is linked to a second targeting agent, and the first binding reagent and the first solid phase are linked via a binding reaction between the first and second targeting agents to form a complex comprising the target analyte bound to the first binding reagent (see e.g., FIGS. 4(a)-4(b)). The complex is then collected and unbound components in the sample are separated from the complex. The complex is released, e.g., resolubilized, and the first solid phase is removed. The released complex is contacted with a second binding reagent bound to a second solid phase, wherein the second binding reagent binds to the complex. The amount of analyte bound to the second solid phase is measured. The detectable label may be attached to any suitable assay component, e.g., the first binding reagent, as in FIG. 4(b), or the third binding reagent, as in FIG. 4(a).

The releasing step in the various assay formats described herein may comprise cleaving a binding reagent from the particle (e.g., as shown in FIG. 1(b)). This may be accomplished by any suitable method, e.g., subjecting the complex to increased temperature, pH changes, altering the ionic strength of the solution, competition, and combinations thereof.

If a targeting agent is employed in the assay format, the releasing step comprises disassociating the first and second targeting agents, e.g., by subjecting the complex to increased temperature, pH changes, altering the ionic strength of the solution, competition, and combinations thereof as discussed above.

The measuring step in the various assay formats described herein may comprise any suitable method of measuring the presence of a detectable label in a sample, e.g., optical absorbance, fluorescence, phosphorescence, chemiluminescence, light scattering or magnetism. In one embodiment, the detectable label is an electrochemiluminescent label and the measuring step comprises measuring an ECL signal and correlating that signal with an amount of analyte in the sample. Thus, the measuring step may further comprise contacting the complex with an electrode and applying a voltage waveform to the electrode to generate ECL.

By analogy to the description of FIGS. 1 and 2, the methods in FIGS. 3 and 4 may also be extended to multiplex measurements, e.g., by employing at least one of the group consisting of i) a plurality of different first binding reagents, ii) a plurality of second binding reagents and iii) a plurality of third binding reagents (the different reagents within (i), (ii) or (iii) being selected for their ability to preferentially bind a target analyte relative to other target analytes). In such multiplex methods, a common targeting reagent pair may be used to link a plurality of different first binding reagents to the corresponding particles or other solid phases. Alternatively, a unique targeting reagent pair may be used for each different first binding reagent (e.g., a different set of complementary oligonucleotides may be used to target each of the different first binding reagents). Such an approach may be used to i) target different first binding reagents to different distinguishable particles (e.g., particles bearing distinguishable labels) or ii) enable multiplexing through the use of a plurality of different second binding reagents, each of which binds preferentially to a different first targeting agent (thus preferentially binding complexes comprising one of the plurality of analytes)

EXAMPLES

Example 1

Figures 5A, 5B:
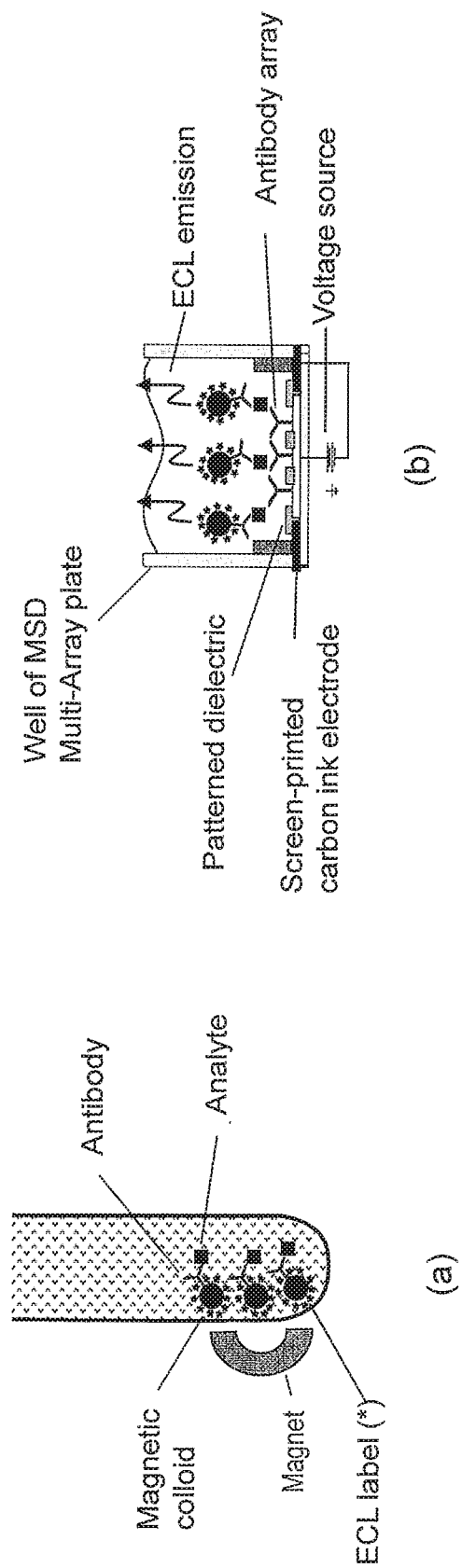
FIGS. 5(a)-5(b) illustrates one embodiment of the present invention.

Dual Use of Labeled Magnetic Particle to Concentrate and Detect Analytes of Interest As shown in FIG. 5, magnetic particles are coated with antibodies against the analytes of interest and a large number (e.g., greater than 100) ECL labels. By attachment of the ECL labels to the antibodies (either before or after coating the antibodies on the particles), very high numbers of labels can be easily achieved. A particle of only 60 nm in diameter can support roughly 160 antibody molecules, assuming about 50 nm$^2$ of surface area per antibody. Thus, attachment of only 1 label per antibody allows labeling ratios of greater than 100 labels per particle to be achieved for 60 nm particles. Labeling ratios of greater than 1000 labels per particle are achieved by increasing the number of labels per antibody and/or increasing the particle size).

A 1 mL or greater volume of sample is combined with the particles in a container and after incubating the mixture to allow the antibodies to bind their respective targets, a magnetic field is applied such that the magnetic particles collect on a surface in the container (a variety of commercial magnetic tube holders or probes are available for carrying out this step). The complexes are washed with buffered saline to remove unbound components of the sample. The magnetic field is removed and the particles are then re-suspended in 100 uL of a suitable assay diluent, thus providing a 10-fold or greater increase in concentration relative to the original sample. The particle-analyte complexes are transferred to an assay plate (e.g., a MULTI-ARRAY® 96-well assay plate, Meso Scale Diagnostics, LLC, Gaithersburg, Md.) that includes a binding surface comprising an array of antibody binding reagents directed against the analytes of interest. Complexes that bind the array are measured by ECL on a SECTOR® Imager instrument (Meso Scale Diagnostics, LLC). The magnetic collection step provides for improvements in assay performance by allowing for pre-concentration of analyte into a small volume and removal of potential interferents in the sample.

Example 2

Assay Using Antibodies Coupled to Magnetic Particles Through Oligonucleotide Hybridization Reactions Magnetic particles are coated with oligonucleotides and a large number (greater than 100) ECL labels. Conjugates are formed comprising antibodies against analytes of interest and oligonucleotides complementary to the oligonucleotides on the particles. The antibody conjugates and particles are subjected to conditions sufficient to hybridize the complementary oligonucleotide sequences (e.g., appropriate temperature, ionic strength and denaturing conditions, as described hereinabove) and thereby coat the antibodies on the particles. These particles are then used to assay for analytes of interest as described in Example 1.

Example 3

Demonstration of the Release of Antibodies Coupled to Magnetic Particles Through Oligonucleotide Hybridization Reactions Magnetic beads (Dynalbeads® MyOne™-Streptavidin C1 beads, Invitrogen Corporation) were coated with a biotinylated oligonucleotide by the following procedure: The beads (3 mg) were washed three times at 60° C. in hybridization buffer (20 mM Tris, 1 mM EDTA, 250 mM NaCl, 0.01% Triton-X at pH=8 and 0.1% BSA). The beads were then coated at room temperature with 750 pmoles of a 19-mer biotinylated oligonucleotide (Oligo 1, Tm=40° C.), in 1 mL of hybridization buffer, for one hour with gentle mixing. The coated beads were washed 5× with hybridization buffer at 60° C. and then resuspended in hybridization buffer at a final concentration of 10 ug/mL. The magnetic beads were then coated with labeled mouse immunoglobulin by the following procedure: Mouse immunoglobulin (mIgG) was labeled with Sulfo-TAG™ ECL labels (Meso Scale Diagnostics, LLC.) according to the manufacturer's instructions. The protein was also labeled with an oligonucleotide having a terminal thiol group (Oligo 2, the complement of Oligo 1) using a bifunctional coupling reagent (sulfosuccinimidyl 4-(N-maléimidométhyl)-1-cyclohexane carboxylate ("SMCC")) and conventional coupling protocols, e.g., protein is reacted with the NHS-ester in SMCC to label the protein and the resulting complex is reacted with thiolated oligonucleotides which reacts with the maleimide group in SMCC. The labeled mIgG-oligo conjugate (0.1 pmol) was then mixed with the oligo-coated magnetic beads (500 ug of beads) in hybridization buffer for 1 hour at room temperature to hybridize the complementary oligonucleotide sequences and thereby immobilize the mIgG onto the beads. The resulting antibody-coated beads were washed and resuspended in hybridization buffer.

The beads were incubated under different conditions, including incubating the suspension at room temperature for one hour (with or without the presence of free Oligo2 as a competitor) and incubating the suspension at 60'C for 10 min. (with or without the presence of free Oligo2 as a competitor). The beads were then magnetically collected and the supernatant analyzed by ECL assay to measure the amount of labeled mIgG that was released from the beads. To measure the labeled mIgG, the supernatant was transferred to the well of a MULTI-ARRAY plate in which the electrode is coated with goat anti-mouse antibodies (MULTI-ARRAY GAM Plate, Meso Scale Diagnostics, LLC.). The plate was incubated with shaking during which time labeled mIgG in the solution bound to the immobilized goat anti-mouse antibodies. The wells were washed with PBS, filled with 150 uL of Read Buffer T (Meso Scale Diagnostics) and analyzed on a SECTOR Imager instrument.

Table 1 shows that, in the absence of competing oligonucleotides, the linkage of the mIgG to the beads was stable at room temperature. The mIgG could be efficiently released from the beads by exposure to short periods of time above the melting temperature of the Oligo1-Oligo2 pair. The efficiency of release could be further enhanced by addition of free Oligo2 as a competitor.

TABLE 1

Efficiency of different release techniques.

| Release Technique | % of Released Material |
| --- | --- |
| 1 H at RT | 6% |
| 1 H at RT with free Oligo | 23% |
| 10 min 60 C. | 50% |
| 10 min 60 C. with Free Oligo | 57% |

Example 4

Assay Including Capture of Analyte Through Collection of Magnetic Particles and Release by Denaturation of a Linkage Comprising an Oligonucleotide Pair Magnetic beads (Dynalbeads® MyOne™-Streptavidin C1 beads, Invitrogen Corporation) were coated with biotinylated oligonucleotides as described in Example 3. The magnetic beads were then coated with antibodies against human TNF-alpha and IL-5 using i) antibodies that were labeled with Sulfo-TAG and Oligo1 and ii) the coating procedure of Example 3.

Assay Procedure with Pre-Concentration. Sample containing human TNF-alpha or IL-5 (1 mL of sample) was combined with 200 ng of antibody-coated beads (prepared as described above) and incubated for 1 hr at room temperature. The beads were magnetically collected and washed with hybridization buffer. The antibody on the beads (including any labeled-antibody-analyte complexes that were formed during the incubation) were released into 100 uL of a 1:20 dilution of hybridization buffer (~10 mM salt) at elevated temperature (60° C.), i.e., by denaturing the oligonucleotide pairs linking the antibodies to the beads. The resulting solution was transferred to a well of a MULTI-ARRAY 96-well plate, each well of which included an array of capture antibodies including an anti-TNF-alpha spot and an anti-IL-5 spot. The plate was incubated with shaking for 1 hr at room temperature to allow the labeled-antibody-analyte complexes to bind to the appropriate capture antibody spots. The wells were then washed three times with PBS and then filled with 125 uL of Read Buffer T (Meso Scale Diagnostics) and read on a SECTOR Imager instrument. The instrument measures and reports the ECL intensity from each array element (or "spot") in the antibody array.

Conventional Immunoassay Protocol without Pre-Concentration. Sample containing human TNF-alpha or IL-5 (30 uL) was combined with 20 uL, of a solution containing labeled (Sulfo-TAG) detection antibodies at a concentration of 1 ug/mL. The resulting solution was incubated for 1 hr in a well of a MULTI-ARRAY plate having anti-TNF-alpha and anti-IL-5 spots. The wells were washed, filled with Read Buffer T and analyzed in a SECTOR Imager instrument as described for the protocol with collection and release.

Results. The results presented in Table 2 show that the protocol with collection and release provided specific assay signals for both TNF-alpha and IL-5 (signal in the presence of analyte—signal in the absence of analyte) that were substantially higher than those obtained using the conventional protocol, without any substantial change in the background signal in the absence of analyte. The enhancement in specific signal for 10 pg/mL samples was greater than 5-fold for TNF-alpha and greater than 10-fold for IL-5.

TABLE 2

| | Assay | | | |
| --- | --- | --- | --- | --- |
| Analyte | TNF | | IL-5 | |
| Concentration, pg/mL | Conventional | Pre-Concentration | Conventional | Pre-Concentration |
| 0 | 371 | 398 | 22 | 27 |
| 1 | 530 | 1,095 | 95 | 451 |
| 10 | 3,301 | 18,323 | 723 | 9,831 |
| 100 | 31,005 | 75,864 | 8,057 | 48,895 |

Example 5

Multi-Well Plate

Another embodiment is a multi-well plate comprising at least one well having (1) a binding surface having a first binding reagent immobilized thereon and (2) at least one additional dry reagent, wherein at least one additional dry reagent is a reconstitutable dry reagent that does not contact the binding surface. The multi-well plate may have an electrode surface with a binding surface incorporated in at least one well of the multi-well plate.

Figure 9A:
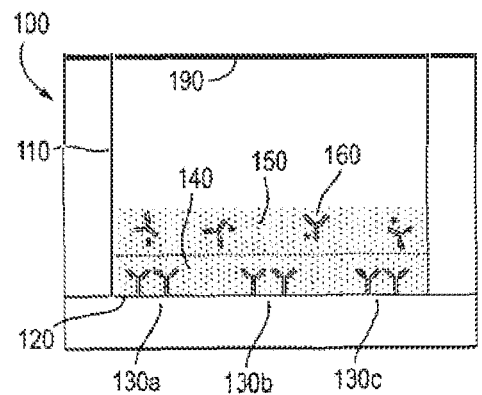
FIGS. 9a-9e show non-scale schematic views of several embodiments of multi-well plate wells that include dry reagents.
Figure 9B:
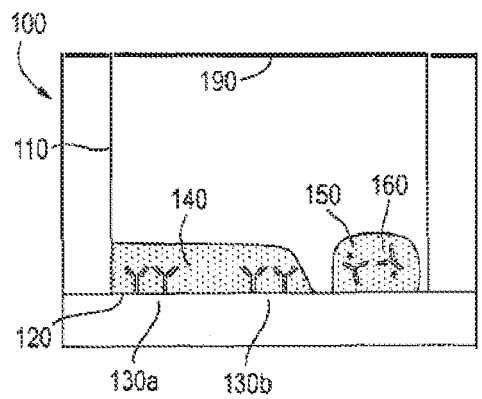
Figure 9C:
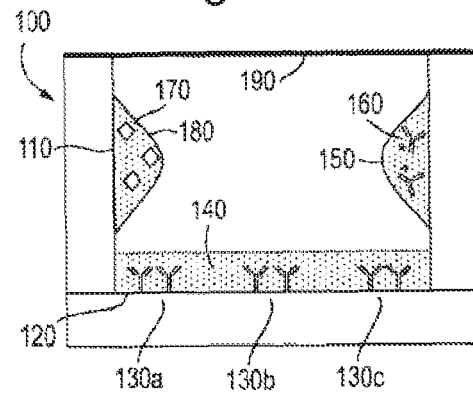
Figure 9D:
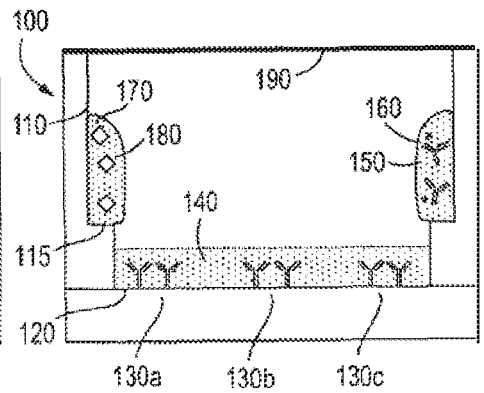
Figure 9E:
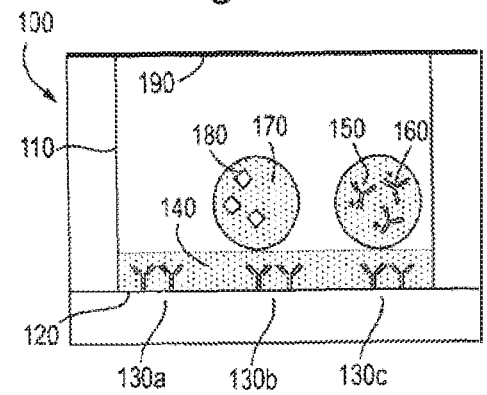

FIGS. 9a-9e show non-scale schematic views of several embodiments of well 100 of a multi-well plate. The well is defined by well floor 120 and well walls 110. Floor 120 and walls 110 may be formed of a single contiguous material or may be separate components (e.g., a plate top and plate bottom) that are mated together. Well 100 also contains a first dry reagent 130 located on floor 120 that, as shown, may be one or more capture reagents that are immobilized on floor 120 to form a binding surface. First dry reagent 130 may include a plurality of immobilized capture reagents (e.g., reagents 130a, 130b, and 130c) that are patterned into a plurality of discrete binding domains (e.g., an array). Advantageously, the binding reagents/domains may have different affinity or specificity for binding partners; such binding domains may be used to carry out multiplexed array-based measurements. A reconstitutable protective layer 140 covers dry reagent 130. Protective layer 140 may be omitted, e.g., when it is not required to physically separate reagents 130 and 150. Well 100 also comprises a second dry reagent 150 that is a reconstitutable dry reagent. Second dry reagent 150 may comprise a detection reagent such as labeled detection reagent 160. Optionally, second dry reagent 150 comprises a plurality of detection reagents that differ in affinity or specificity for binding partners. Well 100 may also include an, optional, additional reconstitutable dry reagent 170 that comprises an assay control analyte 180 (as shown in FIGS. 9c-9e). Also shown is plate seal 190. Plate seal 190, which may be omitted, is sealed against the top surface of walls 110 to protect the dry reagents from the environment.

FIG. 9a shows an embodiment in which first dry reagent 130 is coated with reconstitutable protective layer 140. Second dry reagent 150 is layered onto of protective layer 140 which prevents second dry reagent 150 from contacting first dry reagent layer 130. In one example of this embodiment, second dry reagent 150 is deposited by dispensing it in liquid form on protective layer 140; protective layer 140 is chosen to have enough thickness or mass such that it can adsorb this liquid without allowing it to contact dry reagent 130. The liquid is then dried to form second dry reagent 150. In an alternate example, protective layer 140 is introduced in liquid form and frozen in the well to form a first frozen layer. Reagent 150 is then introduced in liquid form and frozen as a second frozen layer over the first frozen layer. Lyophilization of the two frozen layers provides the layered dry reagent structure.

FIG. 9b shows an embodiment where reagents 130 and 150 are both fixedly located on non-overlapping regions of floor 120. Additional dry reagents, such as assay control reagents (not shown), could be located on other non-overlapping regions of floor 120. The localization of reagents on selected regions of floor 120 may be carried out using standard techniques in patterned reagent deposition or dispensing. Optionally, floor 120 has relatively hydrophilic domains surrounded by relatively hydrophobic areas such that appropriate volumes of reagents dispensed on the hydrophilic domains will spread to defined boundaries determined by the hydrophobic areas. In this and other embodiments where reconstitutable dry reagents are located on a surface, one may pre-treat the surface with blocking agents to prevent adsorption of the reagents to the surfaces and/or include blocking agents in the reagent composition.

FIG. 9c shows an embodiment where second dry reagent 150 is fixedly located, as one or more dry reagent pills, on walls 110. The pills may be formed, e.g., by dispensing one or more droplets of the reagent (in liquid form) on walls 110 and drying them to form the dry reagent pills. FIG. 9c also shows optional additional dry reagent 170 with control analyte 180 fixedly located on another non-overlapping region of walls 110, FIG. 9d shows an embodiment that is like that shown in FIG. 9c except that reagents 150 and 170 are located on shelves 115 on walls 110. Dry reagents 150 and 170 may be formed from liquid reagents by dispensing and drying them on shelves 115 or dispensing them above shelves 115 so that they run down walls 110 onto shelves 115 where they are dried. Alternatively, free-standing dry reagent pills may be placed on shelves 115.

Finally, FIG. 9e shows an embodiment where reagent 150 and optional reagent 170 are free standing dry reagent pills. Also included are embodiments of well 100 in which there is some combination of reconstitutable dry reagents on the well floor, well walls, well shelves, and/or in free-standing form. In alternate embodiments, some combination of fixedly located and free standing reconstitutable dry reagents is employed.

As shown in the embodiments in FIG. 9a-9e, the multi-well plates include those having wells with multiple, physically-distinct, dry reagents. Similarly, for carrying out different assays in different wells, there may be different dry reagents in different wells. It may be desirable, for example for QC purposes, to be sure that the correct dry reagents are present in the wells of a plate. Accordingly, the dry reagents may include indicators (such as dyes or fluorophores) that can be used in optical inspection of the plates. By using different distinguishable indicators in different dry reagents, it is possible to optically inspect a plate to ensure that the correct reagents are in the appropriate locations in the appropriate wells of a plate.

Figure 10A:
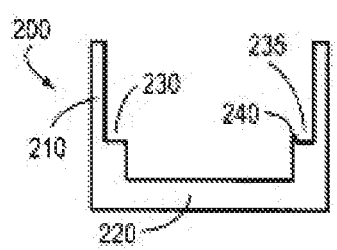
FIGS. 10a-10j show non-scale schematic top and cross-sectional views of several embodiments of wells having walls with shelf elements including ledges (FIGS. 10a-10f), bridges (FIGS. 10g-10h) and tables (FIGS. 10i-10j) that may be used to support dry reagents.
Figure 10B:
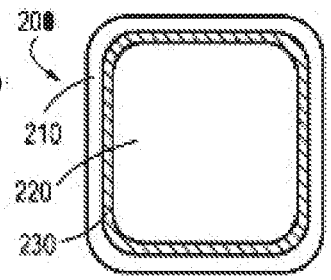
Figure 10C:
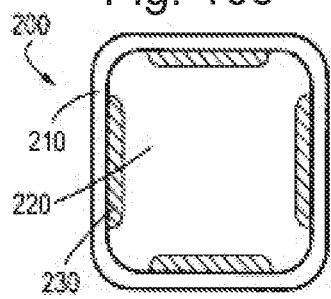
Figure 10D:
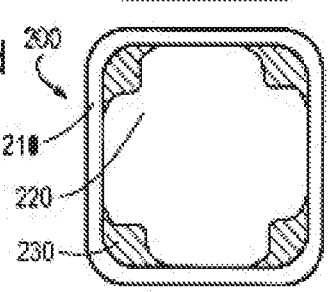

FIGS. 10a-10j shows non-scale schematic views of several embodiments of wells that have shelf elements on which liquid reagents can be held and dried and/or on which free-standing dry reagents may be supported above the well bottom. The shelf elements may include ledges, bridges or tables as described below. FIG. 10a is a cross-section of a well 200 showing well bottom 200 and well wall 210, the well wall having ledges such as ledges 230 and 235 that can support dry reagents. Ledge 230 has an angle that is substantially 90° or less than 90° relative to the wall directly above the ledge such that an appropriate volume of reagent can be dispensed on ledge 230 and accumulate on ledge 230 without overflowing onto well bottom 200. The ledges may also have additional features to help contain reagents such as lip 240 on ledge 235.

Shelf elements such as ledge 235 may be located at any height ($h_s$) above well bottom 240 ($h_b$=0) and below the height of the well ($h_w$). In some embodiments, $h_s$ is greater than or equal to 0.02 $h_w$, 0.05 $h_w$ or 0.1 $h_w$ but less than or equal to 0.1 $h_w$, 0.25 $h_w$ or 0.5 $h_w$. In other embodiments, $h_s$ is greater or equal to about 0.1 mm, 0.2 mm, 0.5 mm, or 1 mm but less than or equal to about 1 mm, 2 mm, or 5 mm. Through proper selection of shelf height and volumes of sample/reagent added during the course of an assay, it may be possible to control the order or timing of assay reactions. In one example, the shelf height and sample volume are chosen such that addition of sample to the well provides a height of liquid that contacts reagents on the bottom of the well and also reconstitutes reagents on one or more shelves. Alternatively, shelf height may be chosen so that addition of defined volume of a first liquid contacts dry reagents on the bottom of the well (reconstituting reconstitutable reagents on the bottom and/or allowing reactions to proceed involving reagents stored on the bottom) but does not reach the height of one or more shelves. Reactions involving reagents on the shelves can be commenced at a later time by adding sufficient volume of a second liquid so that the liquid level reaches the height of the shelves so as to reconstitute dry reagent on the shelves, in conducting an assay, the sample to be measured may be the first liquid, second liquid or both.

Figure 10E:
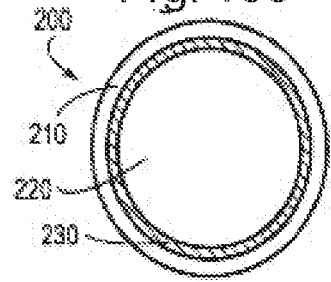
Figure 10F:
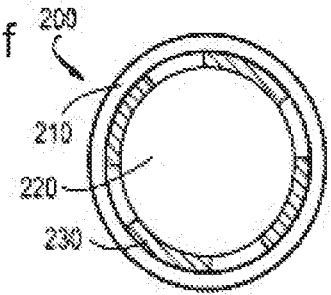
Figure 10G:
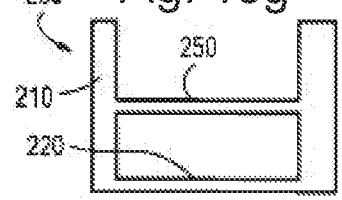
Figure 10H:
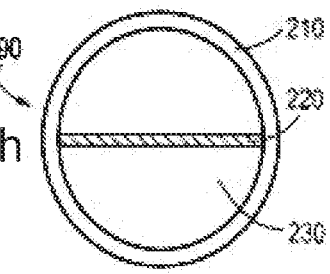
Figure 10I:
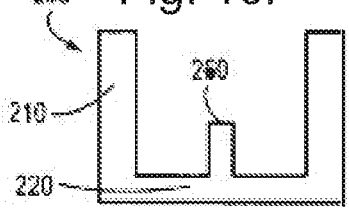
Figure 10J:
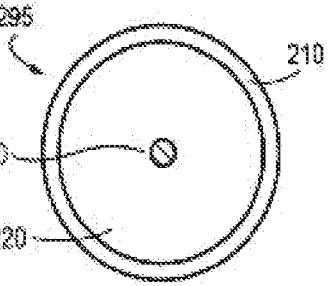

FIGS. 10b-10f show top views of several embodiments of well 200 and show that the well openings may have a variety of shapes including, but not limited to, square (FIGS. 10b-10d) and round (FIGS. 10e-10f). Furthermore, the shelf elements may extend around the perimeter of the well as in FIGS. 10b and 10e or there may be one or more isolated shelf elements that only extend partially around the well as in FIGS. 10c-20d and 10f. A well may also include a plurality of shelf elements at different heights within a well. FIGS. 10g-10h show cross-section and top views, respectively, of a well 290 in which a shelf element is provided by bridge 250 that extends across the well. FIGS. 10i-10j show cross-section and top views, respectively of a well 295 in which a shelf element I provided by a table 260 that extends vertically from an area of well bottom 220.

A multi-well plate is provided comprising a plate body with a plurality of wells defined therein including: a) a plurality of first reagent wells holding a reconstitutable first dry reagent and b) a plurality of second reagent wells holding a second dry reagent (which may be a reconstitutable dry reagent or an immobilized reagent), wherein, the first and second reagents are matched reagents for conducting an assay (i.e., they are both used in conducting an assay of interest). The reagents may be located in a variety of locations with the wells such as well bottom, well walls, on shelf elements, as free-standing pills or powders, etc. A method is provided for carrying out assays in these plates comprising: a) adding a sample to one of the first reagent wells, b) reconstituting reconstitutable dry labeled detection reagents in the first reagent well to form a reaction mixture, c) transferring an aliquot of the reaction mixture to one or more of the second reagent wells, and d) incubating the reaction mixture in the second reagent well(s) so as to carry out said assay on said sample. In one embodiment, the multi-well assay plate can be divided into a plurality of sets of wells consisting of one first reagent well and one or more second reagent wells and the method further comprises repeating the process of (a)-(d) for each set of wells.

Figure 11A:
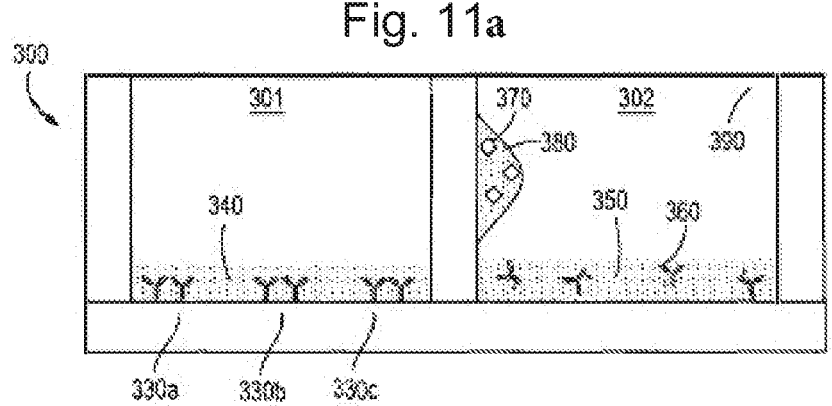
FIGS. 11a-11c show schematic illustrations of multi-well plates having detection wells and reagent reconstitution wells.

FIG. 11a is a (not to scale) schematic illustration of one embodiment showing cross-sectional views of two wells of a multi-well plate 300. Well 302 is a reagent reconstitution well comprising one or more reconstitutable dry reagents which may include a labeled detection reagent (such as dry reagent 350 comprising labeled detection reagent 360) or a an assay control analyte (such as dry reagent 370 comprising assay control analyte 380). These dry reagents may include additional reagent components such as blocking agents, stabilizers, preservatives, salts, pH buffers, detergents, bridging reagents, ECL coreactants and the like. The reagents may be located on well bottoms, specific locations on well bottoms, on well walls, shelf elements or may be free-standing (as per the discussion of FIGS. 9a-9e and 10a-10j). Well 301 is a detection well comprising one or more dry reagents which may include reconstitutable dry reagents or an immobilized dry reagent. As shown, well 301 comprises immobilized capture reagents 330 that are patterned into three binding domains 330a, 330b, and 330c to form a binding surface. Well 301 also comprises a reconstitutable protective layer 340 which may be omitted. In one embodiment of an assay, sample is added to the reagent reconstitution well where reconstitutable dry reagents are reconstituted. The sample is then transferred to the detection well where the assay measurement is carried out. Alternatively, a reconstitution buffer may be used to reconstitute reagents in the reagent reconstitution well; the reconstitution buffer is then combined with sample in the detection well. FIG. 11a also shows plate seal 390 which seals against the openings of wells 301 and 302 to protect the contents of the wells from the environment.

Figure 11B:
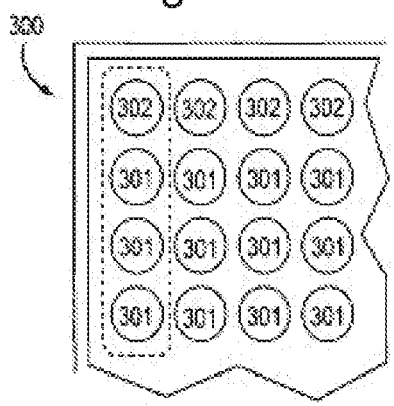
Figure 11C:
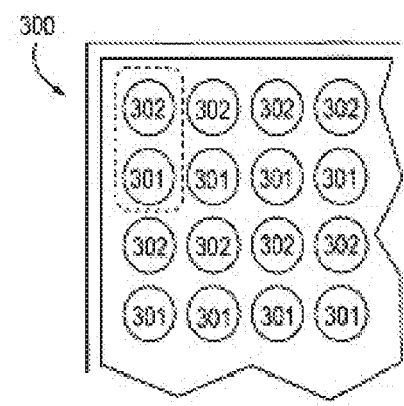

The detection and reagent reconstitution wells in a multi-well plate may be grouped into a plurality of assay sets consisting of one reagent reconstitution well and one or more detection wells, the reagent reconstitution well and detection wells within a set comprising matched capture and detection reagents for measuring an analyte of interest. FIG. 11b shows an arrangement where a set has one reagent reconstitution wells 302 and three detection wells 301. During an assay, a sample added to well 302 may then be distributed among the three associated detection wells 301 so as to conduct multiple replicates or, where the detection wells hold different reagents, multiple different assays. FIG. 11c shows an arrangement where a set has one reagent reconstitution well 302 and one detection well 301.

Figure 12A:
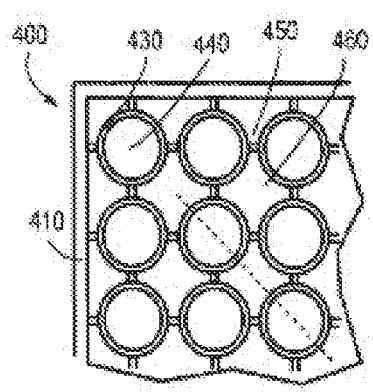
FIGS. 12a-12b show top and cross-sectional schematic views of one embodiment of a plate having detection wells and reagent reconstitution wells, the reagent reconstitution wells being located in interstitial spaces between the detection wells.
Figure 12B:
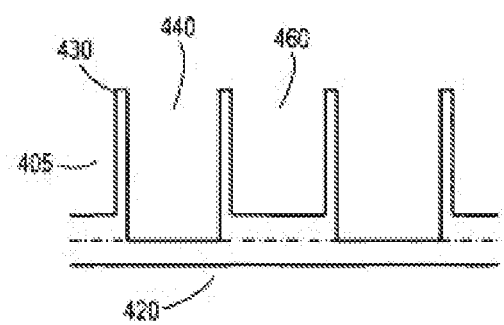

Reagent reconstitution wells and detection wells may be similar in size and shape or may have different sizes and/or shapes. In some embodiment, the wells in a standard multi-well plate are divided between the two types of wells. FIGS. 12a and 12b show a non-scale schematic views of an alternative arrangement of wells. FIG. 12a shows a top view of multi-well plate 400 having detection wells 440 that are arranged in a regular two dimensional pattern and that have detection wells walls 430 with inner wall surfaces and outer wall surfaces. Multi-well plate also has reagent reconstitution wells 460 in interstitial spaces between detection wells. Reagent reconstitution wells 460 have well walls that are defined by the outer well surfaces of detection well walls 430 and rib elements 450 that connect the outer surfaces of well walls 430 of adjacent detection wells (and, in the outermost of the wells, by the inner surface of plate frame wall 410). As shown, the detection wells may be shaped to have no reentrant (i.e., inward pointing) curves or angles while the interstitial wells may have reentrant curves and/or angles. FIG. 12b shows a cross-sectional view along the dotted line in FIG. 12a and shows the bottom surfaces of the two types of wells (which may be at different heights in the plate body). Plate 400 may be formed from a single contiguous material. In an alternate embodiment, plate 400 is formed from a plate top 405 and a plate bottom 420 that are mated along the dotted line shown in FIG. 12b. Advantageously, the basic arrangement of arrays of round wells with interstitial wells defined by the well walls and rib elements is a common feature of many injection-molded 96-well plates and plate tops and allows these components to be used to form dry reagent plates as shown in FIGS. 12a and 12b.

A multi-well plate is provided comprising a) a plate body with a plurality of wells defined therein including: i) a plurality of assay wells comprising a dry assay reagent; and ii) a plurality of desiccant wells comprising a desiccant, and b) a plate seal sealed against said plate body thereby isolating said plurality of wells from the external environment, some embodiments, the assay wells comprise the necessary reagents for conducting an assay in the assay well. Also included are embodiments in which the desiccant wells are connected by drying conduits to the assay wells, the conduits permitting diffusion of water vapor from the assay wells to the desiccant wells but intersecting the wells at a height in the assay well above the location of the dry assay reagent. In addition to multi-well plates containing dry reagents and desiccants, the plates themselves (i.e., without dry reagents and desiccants), in particular, plates having conduit or channel elements (e.g., as shown in FIGS. 13a-

13*f* described below) that are suitable for connecting sets of desiccant and assay wells with dry reagents are provided.

Figure 13A:
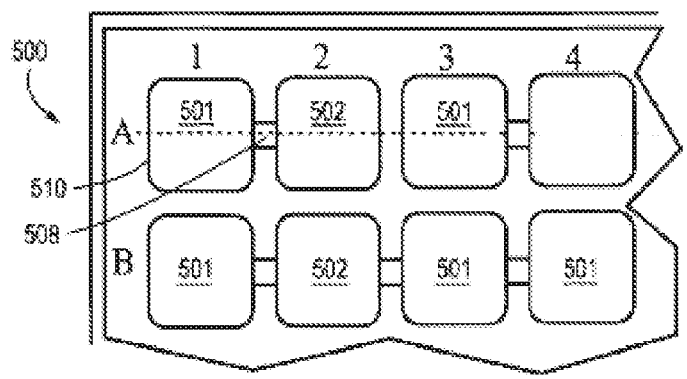
FIGS. 13a-13f show schematic views of multi-well plates 500 (FIGS. 13a-13b), 520 (FIGS. 13c-13d) and 540 (FIGS. 13e-13f) having assay wells and desiccant wells.
Figure 13B:
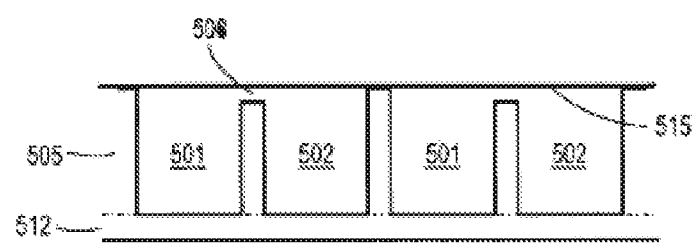

FIGS. 13*a*-13*f* show non-scale schematic views of a multi-well plate 500 having assay wells 501 and desiccant wells 502 (desiccant and dry reagents are not shown). FIG. 13*a* is a top view showing well walls 510 and conduits 508 connecting dessicant wells with one (e.g., as in row A) or more assay wells (e.g., as in row B). FIG. 13*b* shows a cross-sectional view along the dotted line in FIG. 13*a* and together with FIG. 13*a* shows how conduits 508 may be formed by sealing plate seal 515 against channels in the top surface of the plate body. Plate seal 515 seals against these channels and the tops of the wells to form sets of assay and dessicant wells that are interconnected by conduits but are isolated from the environment and from other sets of wells. Accordingly, one or more sets of wells may be unsealed and used in an assay and the remaining sets of wells will be maintained in a dry environmentally protected environment. Plate 500 may be formed from a single contiguous material. In an alternate embodiment, plate 500 is formed from a plate top 505 and a plate bottom 512 that are mated along the dotted line shown in FIG. 13*b*, plate bottom 512 defining the floor of at least some of the wells.

The assay wells or sets of wells in plate 500 may include one or more of any of the dry reagent-containing wells described above, for example, in the descriptions of FIGS. 9*a*-12*b* and may include both detection wells and reagent reconstitution wells. The desiccants used in the desiccant well may be selected from known desiccant materials including, but not limited to, silica, activated alumina, activated clays, molecular sieves and other zeolites, hydroscopic salts (e.g., anhydrous calcium sulfate, magnesium sulfate, sodium sulfate, sodium hydroxide and lithium chloride), hydroscopic solutions (e.g., concentrated solutions of lithium chloride) and water reactive materials such as phosphorous pentoxide. In some embodiments, the desiccant is present as a free dry powder or granular material. In other embodiments, the desiccant is present as a dry pill, for example a pressed tablet or a desiccant impregnated polymeric material. In other embodiments, the desiccant is contained in a water vapor permeable bag or container (e.g., as in commercial silica pouches). Advantageously, desiccant in pill form or pre-packaged containers may be "press fit" into desiccant wells to prevent movement in the well during shipping or use.

Figure 13C:
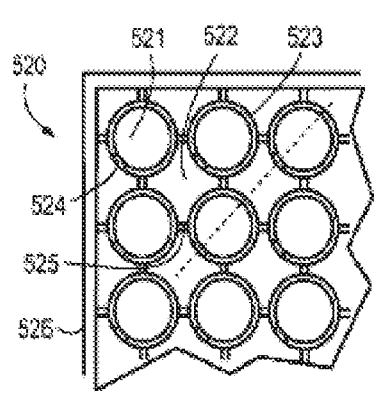
Figure 13D:
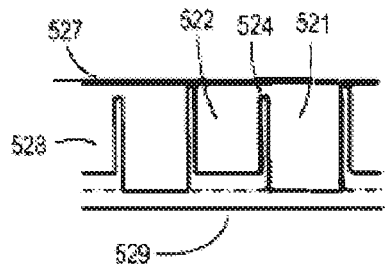

FIGS. 13*c*-13*d* show top and cross-sectional views of one embodiment of a multi-well plate 520 with assay and desiccant wells. Plate 520 has assay wells 521 (which may contain dry assay reagents) that are arranged in a regular two dimensional pattern and that have assay well walls 523 with inner wall surfaces and outer wall surfaces. It also has desiccant wells 522 in interstitial spaces between detection wells (alternatively, wells 521 are used as desiccant wells and wells 522 are used as assay wells). Desiccant wells 522 have well walls that are defined by the outer well surfaces of detection well walls 523 and rib elements 525 that connect the outer surfaces of well walls 523 of adjacent assay wells (and, in the outermost of the wells, by the inner surface of plate frame wall 526). Channels 524 notched into the top of well walls 523 provide, when mated to a plate seal, paths for water vapor to travel from assay wells to desiccant wells. As shown, the assay wells may be shaped to have no reentrant (i.e., inward pointing) curves or angles while the interstitial wells may have reentrant curves and/or angles. FIG. 13*d* shows a cross-sectional view along the dotted line in FIG. 13*c* and shows plate seal 527 which is mated to the top of the plate to form sets of assay and desiccant wells that are connected via conduits 524 but isolated from other wells and from the environment. Plate 520 may be formed from a single contiguous material. In an alternate embodiment, plate 520 is formed from a plate top 528 and a plate bottom 529 that are mated along the dotted line shown in FIG. 13*d*.

Figure 13E:
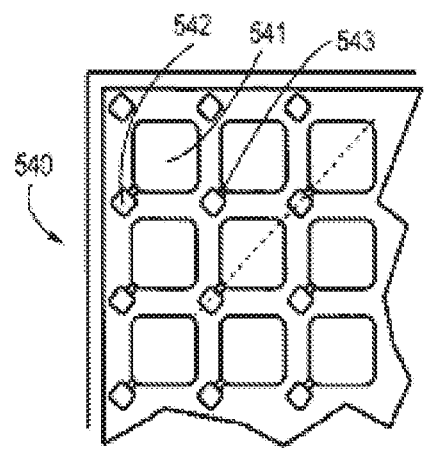
Figure 13F:
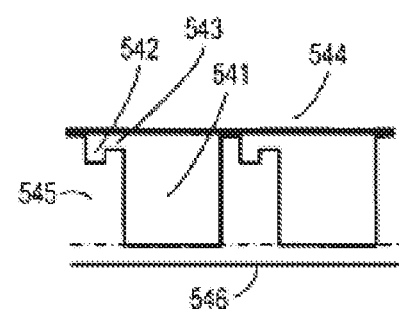

FIG. 13*e* shows a schematic view of another embodiment of a multi-well plate with assay wells (which may contain dry reagents) and desiccant wells and shows a plate 540 with assay wells 541 and desiccant wells 543 that are connected into sets of wells via channels 542 in the plate body. Multi-well plate 540 is largely analogous to the embodiment of plate 500 pictured in FIGS. 13*a*-13*b* except that in plate 540, desiccant wells 542 are much shallower and smaller in area than the assay wells allowing a larger portion of the plate footprint to be dedicated to wells used in assay measurements. FIG. 13*f* shows a cross-sectional view along the dotted line in FIG. 13*e* and also shows plate seal 544 that is sealed against the top of the plate to form connected sets of assay and desiccant wells. Plate 540 may be formed from a single contiguous material. In an alternate embodiment, plate 540 is formed from a plate top 545 and a plate bottom 546 that are mated along the dotted line shown in FIG. 13*f* plate bottom 546 also defining the floor of assay wells 541.

Figure 14:
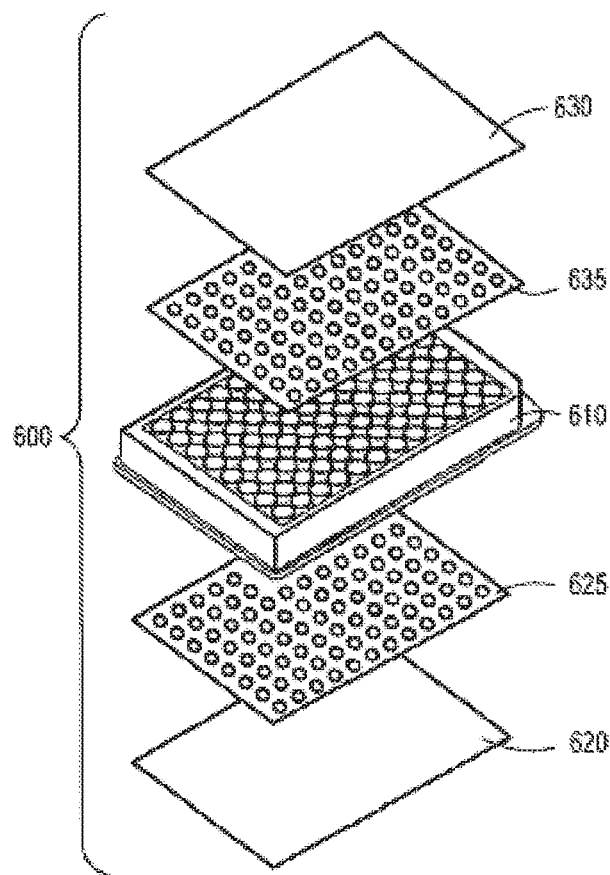
FIG. 14 is a schematic exploded view of one embodiment of a multi-well assay plate.

FIG. 14 is a schematic exploded view of one embodiment of a multi-well assay plate. Multi-well assay plate 600 comprises a plate top 610 with through-holes 615 that define the walls of wells. Plate top 610 is sealed against plate bottom 620 through gasket 625 such that plate bottom 620 defines the bottom surface of the wells. Optionally, plate top 610 is sealed directly to plate bottom 620 and gasket 625 is omitted. Sealing may be accomplished through traditional sealing techniques such as adhesives, solvent welding, heat sealing, sonic welding and the like. In another optional embodiment, plate top 610 fully defines the sides and bottom of the wells and plate bottom 620 and gasket 625 may be omitted. The contents of the wells, which may include wells configured to contain dry reagent and/or desiccant as described above, may be protected from the outside environment by sealing (e.g., via traditional sealing techniques) plate seal 630 to plate top 610 directly or via optional gasket 635.

The components of plate 600 may be made from a variety of different materials including, but not limited to, plastics, metals, ceramics, rubbers, glasses or combinations thereof. In accordance with the requirements of the particular detection technology used with the plates, the components some or all of the components may be selected to be transparent, colored, opaque, or highly light scattering. In one embodiment, plate top 610 is an injection-molded plastic such as injection-molded polystyrene, polypropylene, or cyclic olefin copolymer (COC). Optionally, one or more of the components may be made of or comprise (for example in the form of a coating) a material that has a low water vapor transmission rate, e.g., a water vapor transmission rate less than 1 g/m.sup.2 per day through a 100 um thickness. Low water vapor transmission materials include, but are not limited to, glass, metals or metal films (e.g., aluminum films), COC, polyvinylidene chloride (PvDC), polypropylene, polychlorotrifluoroethylene (PCTFE), and liquid crystal polymers (LCP).

Plate 600 may include desiccant wells as described above. Alternatively, or in addition, desiccant may be incorporated directly into plate top 610, plate bottom 620, plate seal 630, gasket 625 and or gasket 635. For example, U.S. Pat. No. 6,174,952 to Hekal et al. describes desiccant containing polymer blends that may be molded, cast into liners, or formed into films, sheets, beads or pellets.

In some embodiments, plate bottom 620 has features to facilitate the patterning of reagents on the bottom of wells (e.g., patterned hydrophilic features surrounded by hydrophobic areas) and/or conductive layers that provide electrodes that are exposed to the interior volumes of the wells of plate 600 so that electrochemical or electrode induced luminescence assays (e.g., electrochemiluminescence assays) may be carried out. Plate bottom 620 may also include electrode contacts to allow an external instrument to apply electrical potential/current to the electrodes. Suitable approaches, configurations and compositions for such features, conductive layers and electrode contacts include those described in U.S. Publications 2004/0022677 and 2005/0052646 to Wohlstadter et al. Suitable instrumentation and methods that can be used to conduct ECL measurements using assay modules include those described in U.S. Publications 2004/0022677 and 2005/0052646 of U.S. application Ser. Nos. 10/185,274 and 10/185,363, respectively; U.S. Publication 2003/0113713 of U.S. application Ser. No. 10/238,391; U.S. Publication 2005/0142033 of U.S. application Ser. No. 10/980,198; and the concurrently filed U.S. application Ser. No. 11/642,968 of Clinton et al. entitled "Assay Apparatuses, Methods and Reagents."

Figure 15A:
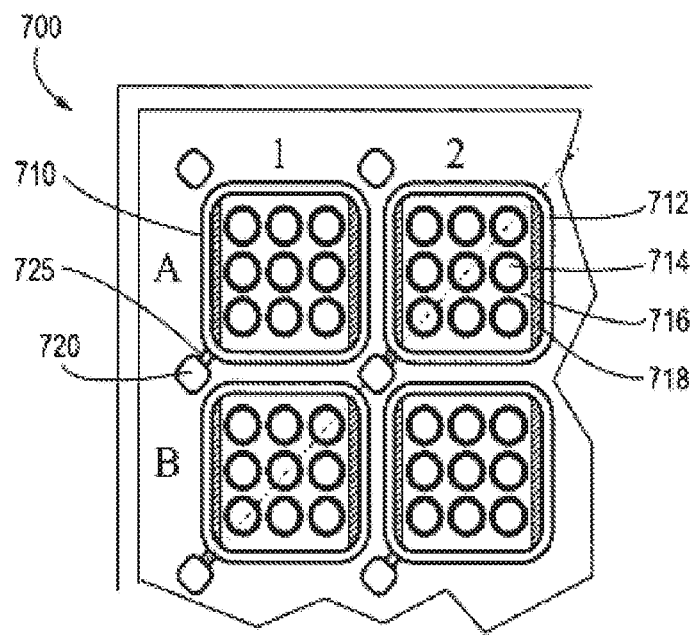
FIGS. 15a-15c show three schematic views of a multi-well plate that is configured to carry out array-based multiplexed electrochemiluminescence assays.
Figure 15B:
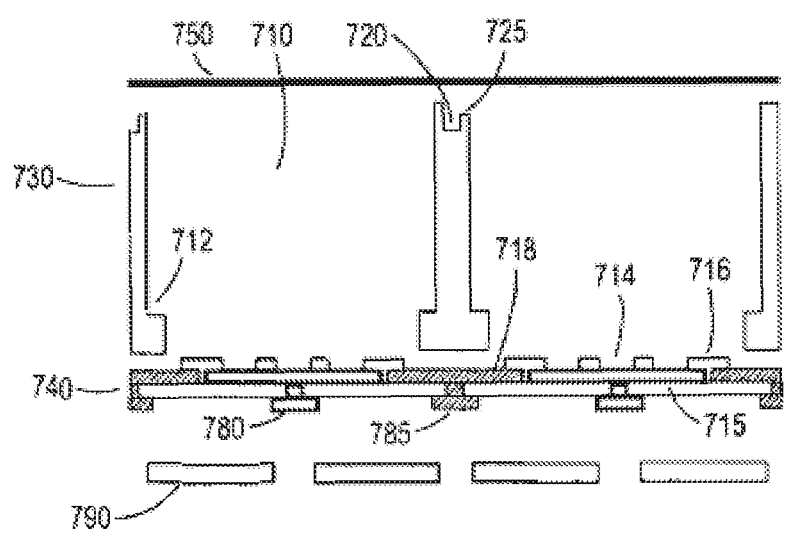
Figure 15C:
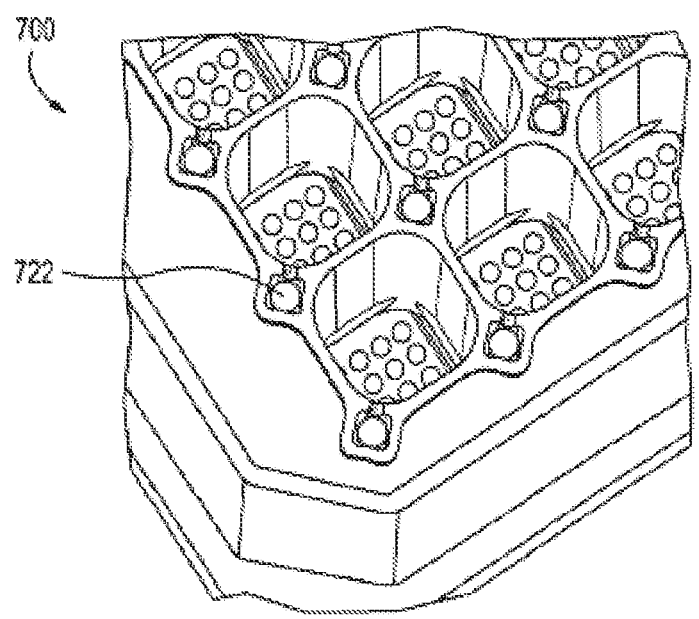

FIGS. 15a-15c provide schematic illustrations of one specific embodiment that includes some of the inventive concepts disclosed above in the context of a multi-well plate configured to carry out array-based multiplexed electrochemiluminescence assays. FIG. 15a shows a section of multi-well plate 700 that has a plurality of assay wells 710 which may comprise dry reagents and a plurality of desiccant wells 720 which may comprise a desiccant. Channels 725 on the top surface of plate 700 link each desiccant well to an assay well. Optionally, desiccant wells 720 and channels 725 are omitted. Assay wells 710 have ledges 712 which may be used to support a reconstitutable dry reagent (e.g., dry reagents comprising assay controls and/or ECL labeled detection reagents). Assay wells also have working electrode surfaces 714 which are covered by patterned dielectric layer 716 so as to expose a plurality of exposed electrode surfaces or "spots" (shown as circles within the wells). In addition, counter electrodes 718 are provided to provide for a complete electrochemical circuit. Optionally, the surface of dielectric layer 716 is hydrophobic relative to electrode surface 714 so that small volumes of reagents patterned onto the spots may be kept confined to the spots. The different spots may have different capture reagents immobilized thereon to form a binding surface with an array of binding domains differing in specificity or affinity for binding partners (e.g., analytes of interest). Alternatively, some of the spots may have reconstitutable dry reagents confined thereon which, e.g., may contain assay controls and/or ECL labeled detection reagents. The assay well may further comprise a reconstitutable protective layer over the binding surface.

FIG. 15b provides an exploded cross-sectional view along the dotted line in FIG. 15a and illustrates one approach to forming the electrode/dielectric layers in assay wells 710. The multi-well plate comprises a plate top 730 that defines desiccant wells 720 and has through-holes that define the walls of assay wells 710 and ledges 712. Plate top 730 also has channels 725 that form conduits between assay wells 710 and desiccant wells 720 when plate seal 750 is sealed against the top surface of plate top 730. In one non-limiting example, plate top 730 is an injection-molded part molded from a plastic with low water vapor transmission. In another non-limiting example, plate seal 750 is a heat sealable film comprising a low water vapor transmission plastic or a metal (e.g., aluminum) foil.

FIG. 15b also shows plate bottom 740 which seals against plate top 730 and defines the bottom of assay wells 710. Plate bottom 740 comprises substrate 715 which supports patterned conductive layers that provide for electrodes 714 and 718. Patterned dielectric layer 716 on the electrodes defines the exposed electrode spots. A variety of materials may be used to provide for the substrate and the conductive and dielectric layers (see, e.g., U.S. Publications 2004/0022677 and 2005/0052646). In one non-limiting example, the substrate is a plastic film (made, e.g., of a polyester such as MYLAR, polyvinylchloride, or a low water vapor transmissive material such as COC), the conductive layers are screen printed conducting inks (e.g., screen printed carbon inks) and the dielectric layer is a screen printed insulating ink. Also shown in FIG. 15b are electrode contacts 780 and 785 which are conductive layers on the bottom of substrate 715 that provide connectivity (e.g., via conductive through holes in substrate 715 to electrodes 714 and 718. The electrode contacts may also be provided by screen printed conductive inks which during printing can be caused to fill holes in substrate 715 to also provide the conductive through-holes. Advantageously, the conductive through-holes may be located directly below well walls to limit water vapor transmission through the holes. In addition, an optional bottom sealing layer 790 may be sealed to the bottom of substrate 715. Bottom sealing layer 790 is made of a low water vapor transmissive material and covers most of the bottom surface of substrate 715 except for defined openings in sealing layer 790 that are located so as to allow a plate reading instrument to contact electrode contacts 780 and 785.

FIG. 15c shows a more detailed angled view of one embodiment of plate 700 and shows desiccant pills 722 that are press-fit into desiccant wells 720.

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. An assay device comprising:
(a) a storage zone comprising a storage surface to which two or more surface-reagent complexes are bound and thereby confined to said storage zone, said two or more surface-reagent complexes comprising a first surface-reagent complex and a second surface-reagent complex, wherein said first surface-reagent complex comprises:
(i) a first reagent linked to a first targeting agent,
(ii) a first surface linked to a second targeting agent, and
said second surface-reagent complex comprises:
(iii) a second reagent linked to a third targeting agent, and
(iv) a second surface linked to a fourth targeting agent,
wherein said first surface and said second surface are portions of the same storage surface, wherein said first reagent and said first surface and said second reagent and said second surface are linked, respectively, in said first and second surface-reagent complexes, via a selective releasable binding interaction between said first and second targeting agents and said third and fourth targeting agents, respectively, wherein said first reagent is configured to release from said first surface-reagent complex by a first set of conditions, and said second reagent is configured to release from said second surface-reagent complex by a second set of conditions, wherein the first set of conditions is different from said second set of conditions; and (b) one or more use zones each configured to use at least one of said first reagent and said second reagent in an assay for an analyte of interest in a sample.

2. The assay device of claim 1 wherein said one or more use zones each comprise an additional reagent used in said assay.

3. The assay device of claim 1 wherein at least one of said first reagent and said second reagent are binding reagents that bind a component of said assay conducted in said use zone.

4. The assay device of claim 3 wherein said at least one of said first reagent and said second reagent are binding reagents, and wherein said binding reagents bind said analyte.

5. The assay device of claim 2 wherein said additional reagent binds said analyte.

6. The assay device of claim 4, wherein said one or more use zones each comprise an additional reagent used in said assay, and wherein said at least one of said first reagent and said second reagent are binding reagents, and wherein said binding reagents bind a complex formed between said additional reagent and said analyte.

7. The assay device of claim 2 wherein said one or more use zones each comprise a solid support and said additional reagent is bound to said solid support.

8. The assay device of claim 1 wherein said at least one of said first and second reagents comprises a detectable label.

9. The assay device of claim 8 wherein said detectable label is an ECL label.

10. The assay device of claim 1 wherein said storage zone and said one or more use zones are in fluidic communication along a fluid path.

11. The assay device of claim 1 wherein said one or more use zones each comprise two or more assay regions each configured to use one of said first and second reagents in one or more assays conducted with said sample in said assay device.

12. The assay device of claim 11 wherein a first assay region of said one or more use zones is configured to conduct an assay for a first analyte of interest in said sample and an additional assay region in said one or more use zones is configured to conduct an assay for an additional analyte of interest in said sample.

13. The assay device of claim 11 wherein a first assay region of said one or more use zones is configured to conduct a first assay for said analyte of interest in said sample and an additional assay region of said one or more use zones is configured to conduct a second assay for said analyte of interest in said sample.

14. The assay device of claim 11 wherein each of said two or more assay regions comprise an additional reagent used in said assay.

15. The assay device of claim 14 wherein said additional reagent is an additional binding reagent.

16. The assay device of claim 11 wherein said one or more use zones each comprise an array of said two or more assay regions.

17. The assay device of claim 1 wherein at least one of said first and second surfaces is a particle.

18. The assay device of claim 1 wherein at least one of said first and second surfaces is roughened such that the surface area accessible to a component capable of binding to said surface is at least three-fold larger than the surface area of a flat surface.

19. The assay device of claim 1 wherein at least one of said first and second surfaces is roughened such that the surface area accessible to a component capable of binding to said surface is at least two-fold larger than the surface area of a flat surface.

20. The assay device of claim 1 wherein at least one of said first and second surfaces comprises a composite material including exposed particles distributed in a matrix.

21. The assay device of claim 20 wherein said composite material comprises carbon particles, graphitic particles, or carbon nanotubes.

22. The assay device of claim 20 wherein said composite is etched.

23. The assay device of claim 20 wherein said surface comprises one or more indentations and/or raised features.

24. The assay device of claim 1 wherein at least one of said first and second surfaces comprises a hydrogel.

25. The assay device of claim 1 wherein said first set of conditions and said second set of conditions are selected from subjecting said storage zone to increased or decreased temperature, pH changes, an electric potential, a change in ionic strength, competition, and combinations thereof.

26. The assay device of claim 25 wherein at least one of said first set of conditions and said second set of conditions is subjecting said storage zone to increased temperature.

27. The assay device of claim 26 wherein said increased temperature exceeds the melting temperature of said binding interaction.

28. The assay device of claim 1 wherein said assay device is a cartridge.

29. The assay device of claim 1 wherein said assay device is a multi-well assay plate and said use zone is positioned within a well of said assay plate.

30. The assay device of claim 29 wherein said storage zone is located on a supplemental surface of said well that does not overlap with said use zone.

31. The assay device of claim 1 wherein said device is configured to conduct a multiplexed measurement.

* * * * *